(12) United States Patent
Peng et al.

(10) Patent No.: US 7,959,900 B2
(45) Date of Patent: Jun. 14, 2011

(54) PARTICULATE MATERIALS AND COMPOSITIONS FOR RADIO THERAPY

(75) Inventors: Yongren Benjamin Peng, Richland, WA (US); Xingye Cherry Lei, Richland, WA (US)

(73) Assignee: XL Sci-Tech, Inc., Richland, WA (US)

( * ) Notice: Subject to any disclaimer, the term of this patent is extended or adjusted under 35 U.S.C. 154(b) by 990 days.

(21) Appl. No.: 10/531,996

(22) PCT Filed: Mar. 7, 2005

(86) PCT No.: PCT/US2005/007201
§ 371 (c)(1),
(2), (4) Date: Apr. 20, 2005

(87) PCT Pub. No.: WO2005/087274
PCT Pub. Date: Sep. 22, 2005

(65) Prior Publication Data
US 2007/0053830 A1    Mar. 8, 2007

Related U.S. Application Data

(60) Provisional application No. 60/549,904, filed on Mar. 5, 2004.

(51) Int. Cl.
*A61K 51/00* (2006.01)
*A61M 36/14* (2006.01)
(52) U.S. Cl. ...................................... 424/1.11; 424/1.29
(58) Field of Classification Search .................. 424/1.29
See application file for complete search history.

(56) References Cited

U.S. PATENT DOCUMENTS

| | | | |
|---|---|---|---|
| 4,789,501 A | 12/1988 | Day et al. | |
| 5,011,677 A | 4/1991 | Day et al. | |
| 6,143,318 A * | 11/2000 | Gilchrist et al. | 424/446 |
| 6,379,648 B1 | 4/2002 | Day et al. | |
| 6,455,024 B1 * | 9/2002 | Glajch et al. | 424/1.33 |
| 6,537,518 B1 | 3/2003 | Gray | |
| 6,589,502 B1 | 7/2003 | Coniglione et al. | |
| 6,716,156 B2 | 4/2004 | Menuhr et al. | |
| 6,746,661 B2 | 6/2004 | Kaplan | |
| 2002/0114763 A1 | 8/2002 | Glajch et al. | |
| 2004/0042582 A1 | 3/2004 | Ein-Gal | |
| 2004/0131543 A1 * | 7/2004 | Wong et al. | 424/1.11 |
| 2004/0197264 A1 | 10/2004 | Schwarz et al. | |
| 2004/0228794 A1 | 11/2004 | Weller et al. | |
| 2004/0258614 A1 | 12/2004 | Line et al. | |

FOREIGN PATENT DOCUMENTS

| | | |
|---|---|---|
| WO | WO 02/065981 | 8/2002 |
| WO | WO 2004/050168 | 6/2004 |

OTHER PUBLICATIONS

Brow et al. (J. Non-Crystalline Solids 1990, 120, 172-177).*
Yashchishin et al. (Glass and Ceramics 1997, 54, 6-8).*
Reidmeyer et al. (J. Non-Crystalline Solids 1986, 85, 186-203).*
International Search Report mailed Jul. 11, 2005 for International Application No. PCT/US05/07201.
Written Opinion of the International Searching Authority mailed Jul. 15, 2005 for international Application No. PCT/US05/07201.
Supplementary European Search Report mailed Aug. 5, 2008 for European Application No. 05732876.7.

* cited by examiner

*Primary Examiner* — Michael G Hartley
*Assistant Examiner* — Melissa Perreira
(74) *Attorney, Agent, or Firm* — Hunton & Williams LLP

(57) ABSTRACT

Timed-bioresorbable particulates, particularly microspheres or fibers, may be used as a vehicle for delivery of radioisotopes, such as Y-90 and Pd-103 for localized radiotherapy, or as an embolic device. These particulates may also be embedded in polymers, or dispersed in injectable gels or other injectable media for the treatment of various cancers. The benefit of bioresorption, the ability to control the ratio of radioisotopes in the particulate, especially the gamma and beta ratios such as In-111/Y-90 ratio in a particulate, and the benefit of non-conductive implants are disclosed.

22 Claims, 14 Drawing Sheets

PARTICULATE MATERIALS AND COMPOSITIONS FOR RADIO THERAPY

CROSS-REFERENCE TO RELATED APPLICATIONS

This application is a U.S. national phase application of PCT International Application No. PCT/US05/07201, filed on Mar. 7, 2005, which claims the benefit of U.S. Provisional Application No. 60/549,904, filed Mar. 5, 2004, the disclosures of each of which are herein incorporated by reference in their entireties.

STATEMENT REGARDING FEDERALLY SPONSORED RESEARCH AND DEVELOPMENT

The development of this invention was supported at least in part by the United States Department of Health and Human Services in connection with Small Business Innovation Research Grants: R43 CA76860, R44 CA76860, R43 CA79225 and R44 CA79225. Accordingly, the United States Government may have certain rights in the present invention.

BACKGROUND OF THE INVENTION

The invention relates to compositions and methods for delivering labeled compositions, including compositions labeled with radioisotopes such as yttrium-90 (Y-90) and palladium-103 (Pd-103), for a variety of medical and research purposes including internal radiation therapy and embolization with or without the incorporation of radioisotopes. For example, internal radiation therapy is successfully used in treating autoimmune disorders such as rheumatoid arthritis and a variety of concerns such as solid tumors associated with liver cancer, prostate cancer, breast cancer and pancreatic cancer.

Treatment of arthritis, to date, includes medical therapy, surgery and total joint replacement. However, all of these procedures have limitations. For example, medical therapy generally targets inflammatory arthritis through a host of chemical agents with varying degrees of effectiveness, whereas surgical synovectomy is effective treatment, but generally last only three to five years before the synovium (inflammed joint tissue) regenerates. Clinical trial data indicates that radiation synovectomy of rheumatoid arthritis is comparable to surgical synovectomy. In particular, radiation synovectomy using e.g. yttrium-90 is effective in suppressing the inflamed synovium and relieving pain. In a published survey conducted from 1991-1993, at least 13,450 different joint injections in 8,578 patients were administered in Europe, and of these injections, Y-90 colloids were used in almost 90% of the medical centers responding to the survey. Rheumatoid arthritis was found to be the most prevalent disease in patients treated (76%), and knee and finger joints were the most frequently treated joints, 46% and 20% respectively. However, due to the lack of an appropriate delivery vehicle, confining the radioisotopes to the joint cavity was not achieved and unacceptable widespread dissemination of the radioisotope throughout the body occurred.

Radiotherapy has also found wide applicability in the treatment of various tumors. For example, there are many types of solid tumors that are resistant to treatment methods other than radiotherapy, such as solid tumors associated with liver, prostate, breast and pancreatic cancers. One effective solid tumor treatment includes internal radiotherapy by means of intra-arterially injected microspheres. As early as the 1960s, inoperable primary pancreatic and liver cancer were treated by the intra-arterial administration of Y-90 ceramic microspheres (supplied by 3M Company).

One example of a microsphere using radioactive yttrium is set forth in Day et al. (U.S. Pat. No. 5,011,677) discloses radioactive glass microspheres wherein the microspheres are completely non-radioactive until irradiated for use in therapy, and becomes radioactive after irradiation in a suitable neutron beam reactor. While Day et al.'s microspheres provide a therapeutically useful dose of radiation and purport to prevent leakage, absent surgical removal, the microspheres remain entrapped in the patient's body. Similarly, Gray (U.S. Pat. No. 6,537,518) discloses radioactive microspheres made of ceramic. However, both lack the ability to offer traceability or other diagnostic function during or after administration of the microspheres. Furthermore, Y-90 microspheres, described by both Gray and Day are not prepared by directly incorporating Y-90 during the formation of the microspheres. Instead, microspheres are prepared using non-radioactive material first. Then, the Y-90 is either attached (e.g., coating) to pre-made microspheres (Gray), or is created within pre-made microspheres by means of neutron irradiation (e.g., Day, Gray).

Thus, to date, the art has attempted to strike a balance between the chemical durability and non-leakage of non-resorbable implants, and the promise of bioresorbable implants that do not require surgical removal. Additionally, there is a need in the art to provide effective imaging, diagnosis and treatment without the interference and health hazards associated with using conductive implants (e.g. gold, silver or platinum wire) when using Magnetic Resonance Spectroscopy (MRS) or Magnetic Resonance Imaging (MRI). There still exists a need in the art for an implant which permits localized delivery of radioisotopes for radiotherapy, without leakage, but which is resorbable, thereby dispensing with the need for choosing between the undesirable choices of either subsequent surgical removal of the implant or leaving the implant in the patient.

SUMMARY AND OBJECTS OF THE INVENTION

The invention provides methods of manufacture, treatment and compositions for an implant which permits localized delivery of labeling agents for therapy and diagnosis. Preferably the labeling agent is a radioactive isotope for radiotherapy incorporated into bioresorbable particulates such that there is minimal leakage of the radioisotope.

Therefore, one aspect of the invention provides a biocompatible implant material which is resorbable, yet retains its chemical and physical integrity for a desired length of time (e.g., usually 10 half-lives of the longest lived radioisotope in the implant), such that a radioisotope or combination of radioisotopes is retained at a desired site, e.g. localized when implanted into a patient. This timed-bioresorption is also useful where implants are used as temporary fluid blockage (embolization) or as resorbable filler to permit tissue in-growth while implant bioresorption takes place.

Another aspect of the invention provides a resorbable implant material comprising a base glass matrix. In another aspect of the invention, the base glass matrix is a glass frit, particulate, microsphere, porous microsphere, hollow microsphere, microcapsule, fiber, short fiber, small rod, or any other glass particle or article.

Another aspect of the invention provides an implant material comprising a base glass matrix which permits controlled release of radiation into a patient, at a site in need of radiotherapy and/or diagnostics through the amount of isotope incorporated into the base glass matrix or the variety of isotopes incorporated into the same base glass matrix.

Another aspect of the invention provides an implant material which permits radiotraceability and diagnostics by incorporating desirable gamma-emitters such as indium-111 (In-111) or Technetium-99m (Tc-99m), along with desired therapeutic radioisotopes such as Y-90, or permits imaging by incorporating imaging enhancer agents such as gadolinium (Gd) and/or iron (Fe) for magnetic resonance imaging (MRI), barium (Ba) and/or zinc for radiographical detection such as x-ray identification.

In another embodiment the radioisotopes (e.g., gamma-emitters and therapeutic radioisotopes) are incorporated into the base glass matrix in appropriate ratios (e.g., 0.5-5 millicurie (mCi) of In-111 per 100 mCi of Y-90) depending on specified dosage and/or imaging requirements.

In another embodiment the implant materials are used to treat a variety of disorders. In a preferred embodiment the implant materials are used for radiation synovectomy of arthritis, such as rheumatoid arthritis. In another embodiment, the implant materials are used in radiation therapy against a tumor such as those associated with liver, prostate, breast and pancreatic cancer.

In another embodiment, the implant is used in radiation therapy against a tumor associated with prostate cancer is non-conductive.

The non-conductive implant may comprise resorbable sutures and radioactive (e.g., labeled with Pd-103, Cs-131, I-125, Au-198, Y-90, or Y-90/In-111) particulates (e.g., microspheres, fibers, short fibers, or small rods) which can serve as a radiographical marker or x-ray opaque marker for the identification of radioactive particulates inside a tumor.

One embodiment of the invention relates to a radioactive resorbable implant material for localized radiotherapy, or radioembolization comprising: (i) a resorbable base glass matrix which is biocompatible; (ii) a radioactive isotope or radioisotope combination incorporated into said base glass matrix; and (iii) an optional nitrogen-rich surface layer formed on the resorbable base glass matrix, the surface layer being of greater chemical durability in mammalian (e.g., human) body fluids than the base glass matrix. In another embodiment, the implant material is a non-radioactive resorbable implant material for localized therapy or embolization comprising: (i) a resorbable base glass matrix which is biocompatible and (ii) an optional nitrogen-rich surface layer formed on the resorbable base glass matrix, the surface layer being of greater chemical durability in mammalian (e.g., human) body fluids than the base glass matrix.

The resorbable materials of the invention may be used for localized radiotherapy (e.g. through injection or surgical implant) in a resorbable implant material comprising a radioactive isotope or radioisotope combination (e.g., Y-90 and In-111) or in combination with a bioresorbable and/or biocompatible polymer or gel or other dispersing media.

Another embodiment of the invention relates to a method of making a radioactive resorbable implant material comprising (i) incorporating a radioactive isotope or a combination of radioisotopes into a matrix precursor; (ii) processing the matrix precursor into a biocompatible bioresorbable glass matrix, such as bioresorbable glass microspheres, or fibers; (iii) nitriding the surface of said bioresorbable glass matrix, if desired, to create a durable surface layer for prevention of any premature start of bioresorption; (iv) dispersing the bioresorbable glass matrix in a bioresorbable and/or biocompatible polymer (e.g., suture) or gel or other dispersing media such as iodized lipiodol for desired radioactivity retention and distribution. For applications where release of radioisotopes is harmful or it is desirable to delay bioresorption, a desirable length of the initial delay in the start of bioresorption is 5 half-lives, 10 half-lives or increments thereof of the longest lived radioisotope in the implant, although the amount of delay (e.g. half-lives) may be altered based on the selection of radioisotopes and/or their combination.

Another embodiment of the invention relates to a method of making a non-radioactive resorbable implant material comprising (i) incorporating a marker or labeling agent into a matrix precursor; (ii) processing the matrix precursor into a biocompatible bioresorbable glass matrix, such as bioresorbable glass microspheres, or fibers; (iii) nitriding the surface of said bioresorbable glass matrix, if desired, to create a durable surface layer for prevention any premature start of bioresorption; (iv) dispersing the bioresorbable glass matrix in a bioresorbable and biocompatible polymer (e.g., suture) or gel or other dispersing media.

The resorbable material of the invention may be administered to a patient in need of diagnosis or therapy through inserting (e.g. surgically or through injection) the resorbable material into the patient at a site in need of therapy diagnosis. In a preferred embodiment, the resorbable material is radioactive.

Other embodiments of the invention are described below. It should be understood that the various compositions described herein may be used in a variety of methods for detecting, analyzing or treating individuals in need radiotherapy.

In a further embodiment, the invention provides a resorbable material for localized radiotherapy comprising (i) a resorbable implant material containing a radioactive isotope, a combination of radioisotopes, and/or elements capable of being converted into a radioactive isotope; and (ii) a resorbable and/or biocompatible polymer, wherein said resorbable implant material is embedded in said resorbable and/or biocompatible polymer.

In a further embodiment, the invention provides a surgical implant comprising a resorbable implant material containing a radioactive isotope, a combination of radioisotopes, and/or elements capable of being converted into a radioactive isotope.

In a further embodiment, the invention provides a method of making a resorbable implant material containing a radioactive isotope or a radioisotope combination comprising: (i) directly incorporating a radioisotope, combination of radioisotopes and/or elements capable of being converted into a radioactive isotope into a bioresorbable base glass matrix during the process of manufacturing the bioresorbable base glass matrix; and (ii) nitriding a surface of the bioresorbable particulates, or nitriding a surface of the bioresorbable glass matrix and irradiating the nitrided base glass matrix to convert selected elements incorporated in the matrix into a radioactive isotope (or nitriding after irradiation).

In yet another embodiment, the invention provides a method of making a resorbable implant material containing radioactive isotopes comprising: incorporating a predetermined amount of a high energy pure beta emitter (e.g., Y-90, P-32, Ho-166 and Sm-153) for radiotherapy and incorporating a predetermined amount of an appropriate energy gamma emitter (e.g., In-111 or Tc-99m) for imaging or diagnostics. In one embodiment, the radioactive isotopes are incorporated directly and homogeneously (i.e., uniformly) into a base glass matrix, and the glass matrix does not need or require activation, e.g., high energy particle irradiation by a neutron beam, an accelerator or other means.

In yet another embodiment, the invention provides a method of making a resorbable implant material containing radioactive isotopes by incorporating image enhancing agents such as iron and/or gadolinium or other agents suitable for MRI imaging and diagnostics.

In yet another embodiment, the invention provides a method of making a resorbable implant material containing radioactive isotopes without melting bulk glasses.

In yet another embodiment, the invention provides a method of making a resorbable implant material (e.g., glass), such as solid, porous, or hollow microspheres by (a) dissolving all glass components into a solution, preferably an acidic solution; (b) forming spherical dry powders; and (c) solidifying the dry spherical powder into solid, porous or hollow microspheres. These steps can be performed as individual steps or integrated in a continuous succession.

In yet another embodiment, the invention provides a method of making a resorbable implant material suitable for embolization of body fluids (e.g., blood) comprising: controlling drying parameters, solidification parameters, and microsphere classification parameters such that a resultant porous or hollow microsphere has density close to that of the body fluid to be embolized (usually between 1.0 to 1.2 grams/mL) and a dimension appropriate for embolizing the body fluid passage leading to diseased tissues.

In another embodiment, the invention provides a method of making a resorbable implant material comprising: encapsulating desirable radioisotopes into a resorbable base glass matrix, and then embedding said base glass matrix into delivery vehicles such as bioresorbable sutures, injectable gels, issue adhesives and other media, such as synovial fluid, saline, and iodized lipiodol. For example, the invention provides delivery vehicles comprising poly-1-lactic acid in the molecular weight range of 30,000 to 500,000, preferably 50,000 to 200,000, or its co-polymers with polymers such as polyglycolic acid.

In another embodiment, the invention provides a method of administering radiotherapy to a patient comprising inserting the implant material made by any of the recited embodiments into a patient, at a site in need of radiotherapy. Sites in need of radiotherapy can include joints, prostate, breast, liver, pancreas, or other sites associated with soft-tissue tumors.

In another embodiment, the invention provides for resorbable implant material comprising a nitrogen rich surface layer, wherein said nitrogen rich surface layer comprises up to about 15 molar % nitrogen.

In another embodiment, the invention provides a method of administering radiotherapy to a patient comprising infusing the implant material of any of the recited embodiments into a patient, at a site in need of radiotherapy by suspending microspheres in viscous medium, preferable pyrogen-free 85% glycerol, iodized lipiodol or other medium.

In another embodiment, the invention provides a method of administering radiotherapy to a patient comprising real-time monitoring of the implant material of any of the recited embodiments comprising: comprising infusing an implant into a patient, permitting progressive infusion or mini-infusions, permitting relocation of injection entry point in between mini-infusions for improving delivery of microspheres to individual tumor sites, preventing excessive lost or migration of the implant during infusion using real-time monitoring and by allowing early aborting of a procedure due to real-time monitoring using either gamma imaging or MRI imaging, permitting convenient control of total injected activity or dose fraction per individual mini-infusion and cumulative total activity or total dose.

In still another embodiment, the invention provides a method of packaging the implant material of any of the described embodiments into 1 mL syringe (or any other suitable syringe) permitting easy, multiple mini-infusion of precise radioactivity and complete delivery of prescribed activity.

In still another embodiment, the invention provides a resorbable implant material comprising a resorbable base glass matrix and further comprising silicate, wherein said silicate is based on $Na_2O$ (22.5 wt %)—CaO (22.5 wt %)—$P_2O_5$ (6wt %)—$SiO_2$ (45wt %) or similar compositions where each oxide content may vary up to 6wt % from the base silicate.

In another embodiment, the invention provides a method of administering radiotherapy to a patient comprising infusing the resorbable implant material of any of the recited embodiments into a patient at a site in need of radiotherapy.

For each of the recited embodiments, the radioactive isotope or combination of radioisotopes is incorporated directly and homogeneously into the base glass matrix at the time of manufacture. Incorporation of radioactive isotope(s) at the time of manufacture eliminates the need for activation, e.g., high energy particle irradiation by a neutron beam, an accelerator or other means. Preferably, the base glass matrix is a silicate, a borate, a phosphate or combinations thereof. In a preferred embodiment the base glass matrix is a phosphate based matrix.

For each of the recited embodiments, the resorbable base glass matrix comprises phosphate in combination with one or more of calcium, zinc, iron, barium, sodium, strontium, magnesium, aluminum, gallium, indium, lithium, potassium, cesium, or rubidium. In another embodiment the base glass matrix comprises phosphate and calcium. For each of the recited embodiments, the resorbable base glass matrix may be phosphate and may further comprise a calcium metaphosphate (CMP) with a calcium to phosphate ratio (Ca/P)=about 0.5, or a calcium phosphate with Ca/P from about 0.33 to about 1.67, and more preferably, Ca/P ratio between about 0.33 to about 1.0. For each of the recited embodiments, the phosphorus in calcium phosphate may be replaced in part or in whole by boron or silicon, individually or in combination.

For each of the recited embodiments, the resorbable base glass matrix may encapsulate radioisotopes or a radioisotope combination (e.g., mixing Y-90 and In-111 in desirable radioactivity ratios). For each of the recited embodiments, the resorbable implant material may contain a trace element such as selenium (e.g., for chemprevention or other non-radiotherapeutic functions). For each of the recited embodiments, the resorbable implant material comprises an optional nitrogen rich surface layer, wherein said nitrogen rich surface layer comprises up to about 15 molar % nitrogen.

For each of the recited embodiments, the resorbable base glass matrix may contain image enhancing agents suitable for MRI imaging and diagnostics such as gadolinium and/or iron.

For each of the recited embodiments, the resorbable compositions described herein are expected to be able to encapsulate all radioisotopes (natural or man-made) at adequate levels of radioactivity for radiotherapy and/or diagnostics. For instance, a non-exhaustive list of radioactive isotopes includes Y-90, In-111, Pd-103, P-32, Cs-131, Sm-153, Ho-166, Tc-99m, Yb-169, Au-198, Re-188, Re-186, Ir-192, Lu-177, Ba-140, Se-72, I-131, I-125, Sr-90, Dy-165, Er, Tl, Sr, and Gd. Preferred combinations include Y-90/In-111, Y-90/Tc-99m, P-32/In-111, P-32/Tc-99m, Ho-166/In-111, Ho-166/Tc-99m, Sm-153/In-111, and Sm-153/Tc-99m. Preferably these radioactive isotopes or radioisotope combinations may be delivered in an amount effective for radiation synovectomy of arthritis, such as in rheumatoid arthritis or an amount effective for radiation therapy of a tumor.

For each of the recited embodiments, the base glass matrix comprises between 0 and 4 molar % of Y-90/Y-89, or up to 50 curies of total radioactivity (from all isotopes) in 100 milligrams of said base glass matrix.

For each of the recited embodiments, the resorbable material may be for instance particulates, microspheres, porous microspheres, hollow microspheres, microcapsules, fibers, short fibers, small rods, or such particulates dispersed in biopolymers such as bioresorbable sutures, or in biocompatible gels or other media. For each of the recited embodiments, the resorbable material is preferably in the form of microspheres, such as porous microspheres or hollow microspheres.

With the foregoing as well as other objects, advantages and features of the invention that will become hereinafter apparent, the nature of the invention may be more clearly understood by reference to the detailed description of preferred embodiments, including the drawings and the appended claims, and is not meant to be limited thereby.

All patents referenced throughout this application are hereby incorporated by reference in their entirety to the extent not inconsistent with the disclosure herein.

BRIEF DESCRIPTION OF THE DRAWINGS

FIG. 1(A) shows typical glass frit of 38 to 75 µm before spheroidization. FIG. 1(B) shows typical microspheres after spheroidization. FIG. 1(C) shows typical microspheres of 38 µm after precision classification. FIG. 1(D) shows typical microspheres of 75 µm after precision classification. The glass composition for the above particles is XLG0158 which contains 1 mol % $Y_2O_3$.

FIG. 2 shows the effect of $Y_2O_3$ content on the properties of calcium metaphosphate glasses.

FIG. 4 shows the roles of individual oxide components in a calcium phosphate glass. FIG. 4(A) highlights the role of $Na_2O$ in influencing the base bioresorption rate and the effect of surface treatment, while FIG. 4(B) highlights the role of ZnO. All microspheres used contain 1 mol % $Y_2O_3$ and were 38-75 µm in size.

FIG. 5 compares release rates of Y-89 and Ca from XLG0157 glass microspheres.

DETAILED DESCRIPTION OF PREFERRED EMBODIMENTS

Figure 1:
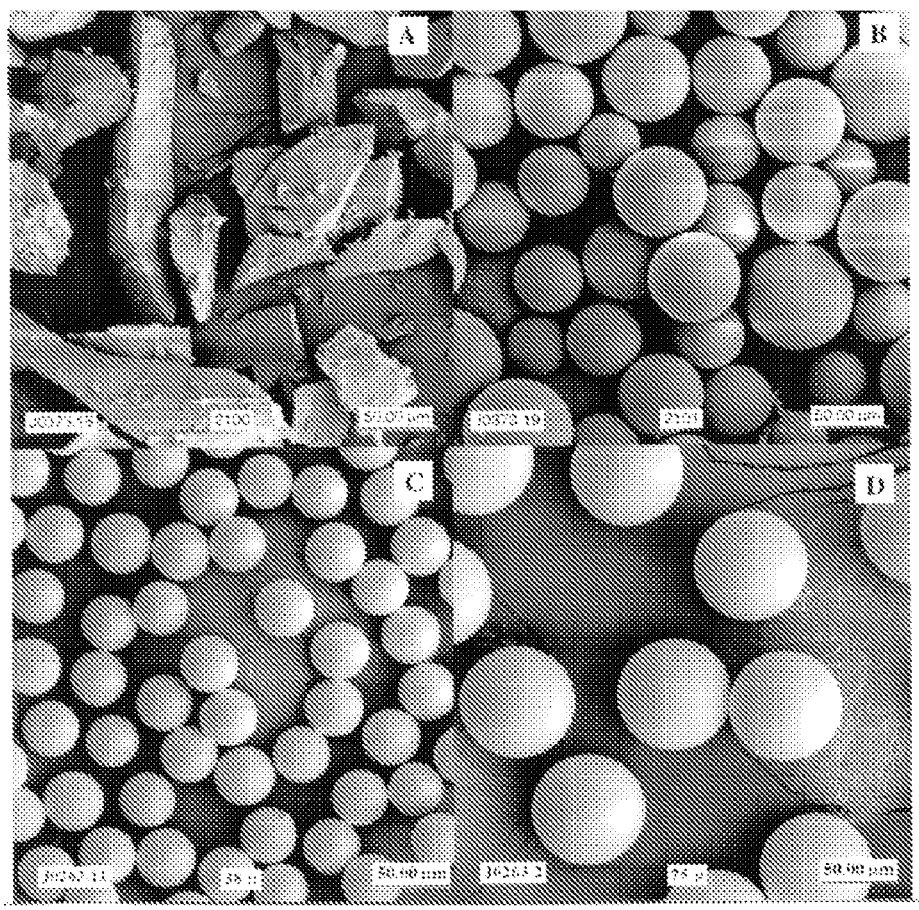
FIG. 1 shows various particles of the invention.

The invention provides the use of timed-bioresorbable implants, preferably particulates such as microspheres or fibers, as a radioisotope delivery system. In particular, phosphate glass microspheres containing a single species of radioisotope (e.g., Y-90), or a combination of radioisotopes (e.g., Y-90 and In-111) have successfully demonstrated the feasibility of timed-bioresorption. In one embodiment, calcium phosphate glasses were melted, processed into microspheres and evaluated. In vitro solutions were analyzed for the release of elements such as yttrium, bioresorption of the microspheres, and for radioactivity leakage from microspheres into the surrounding media. The timed-bioresorption characteristic of glass microspheres was confirmed with three independent measurements, namely, the weight loss of glass microspheres, the release of chemical or radiological elements such as yttrium or Y-90, and the analysis of the chemical makeup of the surface layer of the glass microspheres. Prototypes of the glass microsphere spheroidization setup and the glass microsphere treatment furnace were configured and tested. The doping of radioisotopes such as Y-90, In-111, P-32, Pd-103 into selected phosphate glass microspheres was successful at activity levels suitable for tracer/diagnostics or for radiation therapies. Representative glass microspheres, treated and untreated, containing varied levels of isotopes such as yttrium were also tested and indicated no evidence of toxicity. Stable isotopes are often used with their corresponding radioisotopes to achieve chemical evaluation while minimizing any unnecessary radiological exposure to personnel performing the evaluations. Other aspects of the invention are outlined below:

(i) The resorbable base glass matrix

For each of the recited embodiments any suitable resorbable base glass matrix may be used. The invention employs bioabsorbable glass compositions which are suitable for nitrogen doping. According to the invention, the starting base glass matrix can be made from materials which are (i) resorbable; (ii) biocompatible; (iii) capable of incorporating nitrogen; (iv) capable of encapsulating radioisotopes directly or indirectly (e.g., by means of suitable irradiation); and (v) capable of retaining a radioactive isotope (e.g., prior to base glass matrix being resorbed). Although not so limited, exemplary base glass matrices exhibiting these properties include silicates, borates and phosphates. Specific matrix materials which can be used include calcium phosphates, iron phosphates, zinc phosphates, barium phosphates, or mixed phosphates. The preferred material is calcium phosphates where other additives such as yttrium, palladium, indium, barium, zinc, gadolinium, and iron can be used to adjust bioresorption rates of the base glass or to render traceability, diagnostic function and/or therapeutic function of the particulate implant. In instances where reactive nitrogen-containing species such as ammonia are employed as the vehicle to incorporate nitrogen into the surface of particulates, as described below, the base glass matrix should not include compounds or elements which would form unwanted reaction products when reacted with nitrogen-bearing species. For example, the base glass matrix should not contain high content of lead oxides since lead oxide may be reduced to lead metal causing implant toxicity.

Examples of a "base glass matrix" include a glass frit, particulate, microsphere, porous microsphere, hollow microsphere, microcapsule, fiber, short fiber, small rod, and other glass particles or articles.

Exemplary composition ranges and design principles are listed in Table I. Glasses were prepared using reagent grade chemicals. Care was taken to use the lowest melting temperature possible to minimize volatilization of $P_2O_5$, $B_2O_3$ from the glass melt.

(ii) Radioactive isotopes

For each of the recited embodiments any suitable radioactive isotope or combination of radioisotopes may be used. In addition, for each of the recited embodiments a radioactive isotope or combination of radioisotopes may be incorporated directly and homogeneously into the base glass matrix during the process of manufacturing the implant material. Furthermore, for each of the recited embodiments, the radioactive isotope or a combination of radioisotopes may be incorporated directly and homogeneously into the base glass matrix during the process of manufacturing the glass matrix, wherein the base glass matrix does not need or require activation e.g., by high energy particle irradiation via irradiation by a neutron beam, an accelerator, natural or other means. It will be understood by those of skill in the art that a radioactive isotope or combination of radioisotopes that is incorporated "homogeneously" into the base glass matrix will result in a uniform distribution of said radioactive isotope or combination of radioisotopes in said base glass matrix.

In another aspect, the invention provides embodiments where a radioactive isotope (or a combination of radioisotopes) and an element or elements capable of being converted into a radioactive isotope are incorporated directly and homogeneously into a base glass matrix during the process of manufacturing. In these embodiments, the resorbable base glass matrix may require activation, e.g., irradiation by a neutron beam, an accelerator or other means to convert any stable elements or isotopes into radioisotopes.

Radioactive isotopes that can be used in the invention include yttrium-90 (Y-90), strontium-90 (Sr-90), In-111, Pd-103, P-32, cesium-131 (Cs-131), samarium-153 (Sm-153), holmium-166(Ho-166), technetium-99m (Tc-99m), ytterbium-169 (Yb-169), gold-198 (Au-198), rhenium-188 (Re-188), rhenium-186 (Re-186), iridium-192 (Ir-192), lutetium-177 (Lu-177), barium-140 (Ba-140), selenium-72 (Se-72), iodine-131 (I-131), iodine-125 (I-125), dysprosium-165 (Dy-165), or any other suitable radioactive isotope. Proper mixing of radioisotopes is not only permissible but also desirable. Such mixing or cocktailing of radioisotopes to achieve desired properties may be achieved for example, by mixing homogeneously relatively low activity radioisotopes such as tracers (e.g. gamma-emitting, In-111) with relatively high activity radioisotopes for their therapeutic properties (e.g. pure beta-emitting, Y-90) within each microsphere. Such a combination makes it possible to radio-trace individual microspheres for improving Y-90 activity distribution and Y-90 dose confirmation. Thus, in the above example, In111 acts as tracer while Y-90 delivers the radiation dose. In another non-limiting example, the therapeutic radioisotope can be Y-90 and the tracer can be Tc-99m. Other combinations include P-32/In-111, P-32/Tc-99m, Ho-166/In-111, Ho-166/ Tc-99m, Sm-153/In111, and Sm-153/Tc-99m. A person skilled in the art will readily appreciate other radioisotope combinations can be used. Furthermore, radioisotopes may be introduced with stable (or non-radioactive) isotopes. For example Y-90 (radioactive) may be introduced into base glass matrix in appropriate ratios with stable isotopes such as Y-89 such that the total yttrium as chemical species are maintained in a given range while Y-90 activity can be adjusted depending on the dose requirement. Generally, the radioisotope or radioisotope combination employed must satisfy two criteria. First, it must be one which provides a therapeutic dosage of radiation for treatment (e.g., for cancer), and/or radio-traceability or diagnostics, or other conditions as described below. For example, it is preferred to have a half-life or radiation energy range compatible with its use as an implant for therapy and/or diagnostics. Second, it must be a material which is compatible with the base glass matrix to be effectively encapsulated within it. Since the base glass matrices described in Table I can host all of the radioisotopes listed above, or isotope combinations thereof, it is expected that essentially all radioisotopes (natural or man made) can be encapsulated in one or more base glasses listed in Table I.

Optionally, some radioisotopes may be formed by irradiating elements contained in the base glass matrix. For example, Au-198 or Ho-166 can be formed when natural gold isotope (Au-197) or natural holmium isotope (Ho-165) is irradiated with a thermal neutron beam.

(iii) Nitrogen doping

For each of the recited embodiments of the invention nitrogen doping may be used. The purpose of nitrogen doping is to create an outer high chemical durability layer on the resorbable material which will retain particulate integrity for a period of time corresponding to the effective life of the radioisotope. It will be appreciated that the degree to which the base glass matrix is doped with nitrogen will depend on the half-life of the radioisotope incorporated therein. Thus, a base glass matrix containing a radioisotope with a relatively short half life will require less nitrogen doping than a base glass matrix containing a radioisotope with a relatively long half life. The goal is to provide enough of an outer surface layer of high chemical durability so as to prevent premature release of radioactive isotope.

In general, a nitrogen rich layer is created by a process involving nitriding the surface of a biocompatible resorbable base glass matrix to form a nitrogen-rich surface layer of greater durability than the base glass matrix.

By "nitriding" is meant either chemically reacting or structurally incorporating nitrogen into the base matrix.

By "greater durability" is meant that the nitrogen-rich surface layer exhibits an increased resistance to aqueous or biological breakdown and dissolution in aqueous solutions as compared to the untreated base glass matrix.

By "nitrogen rich" layer is meant a layer that includes an amount of nitrogen which is greater than that found in the untreated base matrix. Generally, the atomic amount of nitrogen incorporated into the surface layer is dependent on the nature of the material employed as the base matrix. Thus, certain base matrix materials can incorporate larger amounts of nitrogen than other base materials. For example, silicon nitride ($Si_3N_4$) incorporates four moles of nitrogen for every three moles of silicon. By contrast, boron nitride (BN) incorporates one mole of nitrogen for every mole of boron. The nitriding of calcium metaphosphate ($CaP_2O_6$ or CMP) results in a matrix having, as the theoretical maximum, two moles of nitrogen which replace three moles of oxygen, for a total of 25 molar % nitrogen. In practice, most matrix materials would include no more than about 25 molar % of nitrogen after the nitriding. Typically, for CMP, there would not be present more than about 15 molar % nitrogen.

A person skilled in the art will readily appreciate that the amount of nitrogen incorporated into the base matrix to form the nitrogen rich layer will depend on factors such as the length of time that it is desired to have an implant retain its structural integrity when placed in a biological environment. Where controlled release of a therapeutic agent is desired, obviously the rate at which it is desired to release such component will determine the amount of nitrogen which is ultimately incorporated into the matrix. By virtue of the invention, it is generally possible to control bioresorption of the base matrix for a time interval ranging from as short as two hours to as long as one year or longer.

In order to carry out the nitriding step, the matrix or particulates are treated with a nitrogen-containing moiety capable of nitriding the matrix or particulates for a time and temperature sufficient to provide a nitrogen rich surface layer of greater durability than the base glass matrix. In this regard, two preferred nitrogen containing moieties are ammonia gas and a nitrogen plasma.

(iv) Activation of the Implant (optional)

For each of the recited embodiments the base glass matrix may be activated, e.g., by irradiation. If a desired radioisotope is not directly incorporated into the base glass matrix, but an isotope capable of being irradiated is directly incorporated in base glass matrix instead, the base glass matrix may be activated by high energy particle irradiation via a neutron beam, an accelerator or other means. Obviously, in view of the relatively short half life of many radioisotopes, it is desirable to carry out the activation as close as possible to the surgical implanting of the material into a patient. Activation is achieved in accordance with techniques well known to persons skilled in the art by high energy particle irradiation. For example, Y-89, Ho-165, Au-197 can all be activated in a thermal neutron beam to Y-90, Ho-166, Au-198 respectively. In some embodiments, the invention discloses methods of directly incorporating radioisotopes into a base glass matrix, e.g., during the process of manufacturing said base glass matrix. If all desired radioisotopes are already incorporated directly into the base glass matrix, then the activation is optional or unnecessary. For example, microspheres or particulates with both Y-90 and In-111 incorporated within said microspheres or particulates will not require activation. However, the invention contemplates embodiments where a radioactive isotope (or a combination of radioisotopes) and one or more isotopes capable of being irradiated are directly incorporated in base glass matrix during the process of manufacturing. In these embodiments, the base glass matrix may require activation, e.g., irradiation by a neutron beam, an accelerator or other means, in order to convert the one or more isotopes capable of being irradiated into radioactive isotopes.

(v) Insertion of implant into a patient

For each of the recited embodiments the implant material may be inserted into a patient. The implant containing the radioisotopes is inserted as needed into a patient. Contemplated uses of the implant include radiation therapy for treatment of tumors as well as treatment of arthritis and other therapeutic needs. For example, the implant with or without radioisotope can be inserted as an embolization implant with or without radiotherapy component. The implants are inserted in accordance with well characterized protocols known in the art.

An exemplary description is given below for liver cancer, prostate cancer and arthritis.

Figure 10:
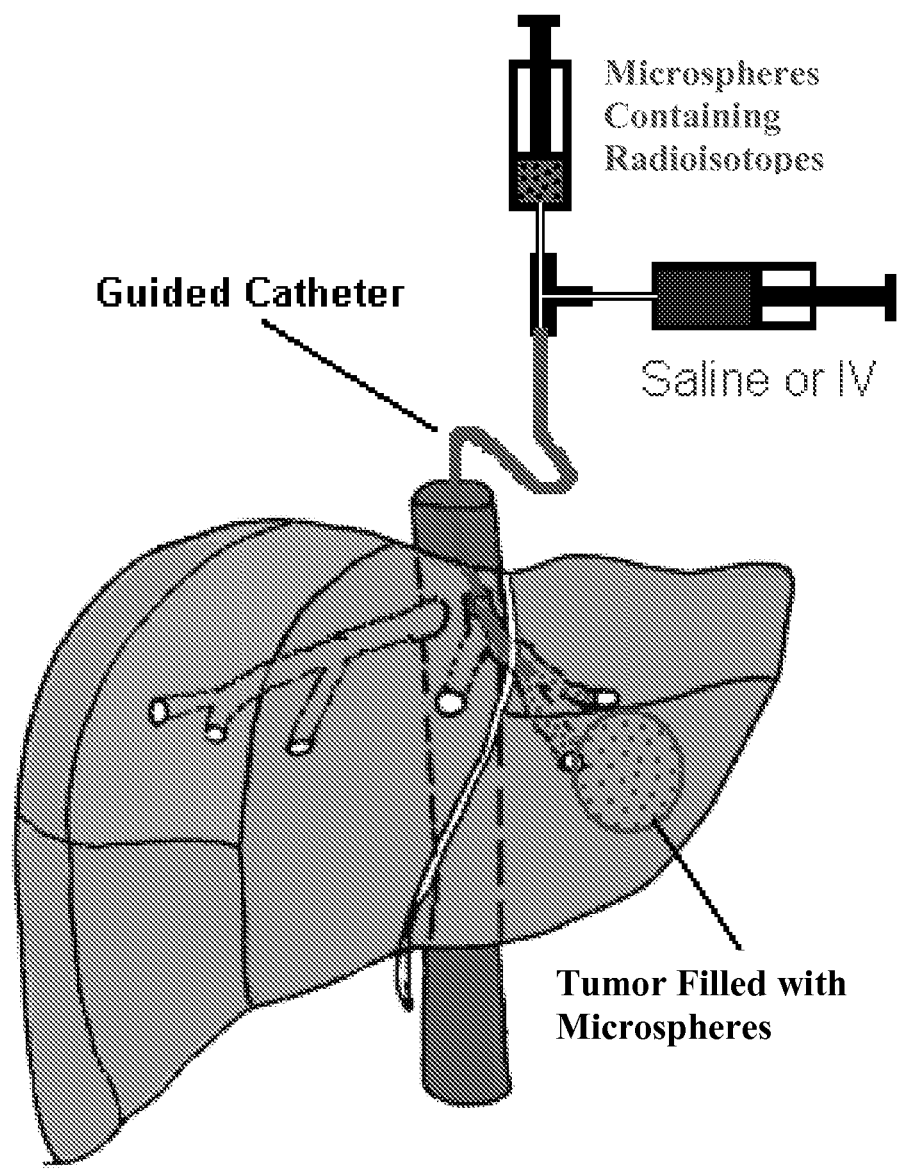
FIG. 10 is a schematic diagram showing microspheres injected into the hepatic artery.

For liver cancer, microspheres are suspended in an injectable medium such as pyrogen-free 85% glycerol or iodized lopiodol and may be packaged in a 1 mL syringe (or any other suitable syringe) with appropriate radiation shielding. Microspheres in the size range of 15 to 80 (preferably 30 to 60) micrometers in diameter are infused into a selected hepatic artery using the appropriate size catheter (e.g., between 3 French and 5 French). The insertion of the catheter, for example, in dogs starts with the femoral artery, and proceeds into the aorta and celiac artery, then into selected hepatic artery or arteries. Insertion of a catheter in a human patient is similar and the catheter size is usually larger. The infusion into the liver can be done in one injection followed by flushing and rinsing with saline solution, or the infusion can be administered in multiple mini-infusions followed by a mini-saline flush. In either case, the last step should be saline flushing in sufficient volume to flush all microspheres out of the catheter before catheter retrieval. The catheter can also be relocated in between mini-infusions for improving delivery of microspheres to the tumor sites. Particulates lodged in the microcapillary bed surrounding the liver tumor can deliver therapeutic radiation. Gamma emitters such as In-111 provide means of tracking the placement and potential migration of the particulates after infusion. Particulates or microspheres are expected to remain in the tumor micro-capillary bed and will then be gradually dissolved and carried away by urine or feces. A exemplary diagram of the infusion is shown in FIG. 10. An important advantage of gamma tracers such as In-111 or Tc-99m in the microspheres is to provide real-time microspheres distribution. In the case of excessive (20% or more, in the judgment of attending physician) microspheres shunting to the lung, the infusion procedure can be stopped, avoiding administrating the entire pre-planned activity to a patient. This is an important safety feature.

For arthritis treatment, particulates may be suspended in injectable medium such as saline, synovial fluid or other injectable media. The injection may be directly into the joints using a small needle or other instrument. The synovial wall or lining is expected to retain the particulates within the joints. Joints may be flexed after injection to ensure uniform distribution of microspheres within the joint fluid. Particulates or microspheres for arthritis are usually small (e.g., less than 15 micrometers, preferably 1 to 5 micrometers in diameter) compared to particulates for liver cancer (between 15 to 80 micrometers, preferably 30 to 60 micrometers in diameter).

For prostate cancer, particulates containing radioisotopes such as Pd-103, Cs-131, I-125, Au-198 are not injected or implanted directly as compared to liver and arthritis treatment. It is recommended that for tumor tissues lack of a lodging mechanism (such as lodging in the capillary bed in the case of a liver tumor) or lack of retaining boundaries (such as in the synovial wall or lining in the case of arthritis), either a retaining mechanism is created within the tissue first, before particulates are placed, or the particulates be retained within a delivery vehicle. Retaining the particulates within a delivery vehicle may be preferred to achieve benefits such as minimally invasiveness, and less complex surgical procedures. Particulates can be embedded in bioresorbable polymers such as polylactic acid or its derivative polymers. Polylactic acid or its co-polymers have been widely used as bioresorbable sutures in surgery. For example, the invention provides delivery vehicles comprising poly-1-lactic acid in the molecular weight range of 30,000 to 500,000, preferably 50,000 to 200,000, or its co-polymers with faster bioresorption polymers such as polyglycolic acid. Continuous and flexible radioactive seeds are made by embedding radioactive particulates (e.g., microspheres, fibers or small rods) in bioresorbable polymers (e.g., poly-1-lactic acid), sutures, or fibers. Such a suture may be cut to a particular length to be placed into the prostate using essentially the same insertion apparatus used for non-resorbable titanium shell based prostate seeds. The bioresorbable polymer composition in the invention will be such that the physical integrity of the polymer will be preserved to retain particulates and the particulate will have no or minimal bioresorption before the complete decay of radioactivity encapsulated within the particulates. More preferably, the biodegradation of the polymer delivery vehicle is in phase with the bioresorption of the particulates, ideally the complete biodegradation of the polymer delivery vehicle will be after the complete bioresorption of the particulates. A person skilled in the art will readily appreciate that the use of radioisotopes with short half-life such as Au-198, Cs-131, Pd-103 enhances the benefit of bioresorption. For example, radioactivity of Pd-103 is typically considered decayed in 80 days and I-125 in 300 days, respectively. Particulates of the invention can serve as radiographical markers or x-ray opaque markers for the identification of radioactive particulates inside a tumor. In general, calcium phosphate particulates, especially particulates containing barium, and/or zinc, have radiographical visibility. The particulates may be microspheres, fibers, short fibers or small rods. Particulates for radiographical visibility can be in the range of 30 to 1000 micrometers, preferably 100 to 1000 micrometers in diameter.

Other delivery vehicles include embedding particulates in a biocompatible gel which retain or restrict the migration of the particulates, or by adhering particulates to tissue adhesives for improving distribution of the particulate and for restricting the migration of particulates, thus achieving higher uniformity of radioisotope distribution and minimizing radioisotope leaking. Other non-conductive delivery vehicles include a poly-1-lactic acid in the molecular weight range of 30,000 to 500,000, poly-1-lactic acid co-polymers with polyglycolic acid, polydioanone (PDS II), polyglycaprone 25 (Moncryl), polyglactin 910 (Vicryl), phenyletheretherketone (PEEK), polysulfone (PSU), polyurethane, polypropylene, silicone, polyethylene terephthalate (PET), polyphenylene oxide blends (PPO), polyphenylsulfone (PPSU), polyether sulfone (PES), polyphenylene sulfide (PPS), polyetherimide (PEI), liquid crystal polymer (LCP), or combinations thereof The most important consideration is the delivery of radioactive particulates to targeted location and ensuring that they remain there without unwanted side effect usually associated with particulate migration.

Thus, one embodiment provides for prostate seeds comprised of bioresorbable radioactive particulates and bioresorbable and/or biocompatible polymers (e.g., poly-1-lactic acid or its co-polymers) both of which are non-conductive (e.g., which eliminate or reduce electromagnetic interference with MRI or other instrumentation) and biocompatible. In this embodiment, the radioactive particulate is preferably embedded in the bioresorbable and/or biocompatible polymers. The particulates are preferably fibers (solid or non-solid) or microspheres (solid or non-solid). Radioisotopes are preferably Pd-103, Cs-131, I-125, Y-90, Y-90/In-111, Y-90/Tc-99m, Au-198 or other isotopes or isotope combinations. A person skilled in the art will readily appreciate other radioisotopes and radioisotope combinations may be used.

In another embodiment, Pd-103 is dissolved and encapsulated in phosphate particulates. The particulates are in turn embedded on hollow polymer tubes made of poly-1-lactic acid in the molecular weight range of 30,000 to 500,000, preferably 50,000 to 200,000. The Pd-103 particulates are conveniently immobilized by heating the hollow tubes to softening temperature to "shringe" the tubes. Radioactive particulates can also embedded in polymers using injection molding or extrusion. Non-conductive and bioresorbable prostate seeds have several major and clearly distinct advantages over non-resorbable conductive seeds such as titanium seeds which are comprised of encapsulating radioisotopes (e.g., Pd-103, I-125) in titanium tubes with both ends sealed by welding. The advantages of using non-conductive and bioresorbable prostate seeds are listed below. While the discussion below uses Pd-103 as an example, other radioisotopes such as Au-198, Cs-131, I-125 can be used in place of Pd-103, especially radioisotopes that are clinically efficacious and have half-lives shorter than that of Pd-103.

1) Post-treatment monitoring and re-treatment options: Subsequent urologic procedures are made simpler since metal components are eliminated and the Pd-103 seeds are completely bioresorbable. The non-conductive nature of timed-bioresorbable Pd-103 seeds will have a great impact in post-treatment identification of any pockets of malignant cells in the prostate, a task that has been very difficult to perform with MR Spectroscopy (MRS) in the presence of metallic titanium seeds due to the interference of metallic seeds with MR signal (electromagnetic intereference). Non-conductive Pd-103 seeds will enable physicians to monitor the tumor post-treatment and anticipate the need for re-treatment of any MRS-positive voxels.

2) Advanced combination therapy with external beam radiation: External beam radiation is a stand-alone treatment option (e.g., requiring 4-5 sessions a week for 6-8 weeks to achieve 144 Gy dose), or can be used as pretreatment with seed boost to follow. Non-conductive timed-bioresorbable seeds can be used as primary treatment with external beam radiation as supplement or "touch up" post-treatment. Timed-bioresorbable Pd-103 seeds are compatible with one particularly attractive AC electromagnetic body navigation or localization technology for directing external beam radiation. Any "cold spots," geographic misses, or any pockets of malignant cells in the prostate can be precisely marked and registered with such a navigation system for directing external beam radiation for "touching up." This advanced combination is ideal and is only possible with non-conductive Pd-103 seeds.

3) Complete bioresorption: The complete bioresorption of the seeds also potentially minimize or eliminate the possibility of secondary cancer associated with permanent titanium seeds. Timed-bioresorbable Pd-103 seeds have potential to become preferred brachytherapy seeds for prostate and other cancers (e.g., breast cancer).

4) No loose seeds and simpler procedure: Timed bioresorbable prostate seeds can be embedded into bioresorbable PLA (polylactic acid) suture to form a semi-rigid and continuous bioresorbable composite seed train, which can be cut to a desired length. It is also possible to produce an individual seed composite (i.e., seed embedded in PLA spacer) to permit intra-operative/real-time dosimetry, since the length of the spacer portion can be adjusted easily and conveniently. A composite seed can be loaded more conveniently and correctly, and is expected to have less mobility compared to a separate seed and spacer. The polymer embedding and the bioresorption of the seeds will completely eliminate the reported high occurrence of permanent titanium seed migration leading to pulmonary embolism.

The invention will now be further described with reference to an exemplary preferred system, employing calcium phosphate as the base matrix material.

A) Glass Formulation:

Calcium phosphates with a wide range of Ca/P ratio (0.3 to 1.67) are generally suitable as matrices for radioisotopes. Calcium metaphosphate (Ca/P=0.5) was employed in the examples which follow for the incorporation of various cations including yttrium isotopes, other isotopes or isotope combinations. Some glass microspheres prepared contained up to 4 mol % (6.5 wt %) of yttrium (potentially higher). Such a high solubility of yttrium in the calcium phosphate microspheres permits the delivery of an extremely high Y-90 radioactivity. The chemical yttrium content in a glass formulation can be maintained at a pre-determined level for maintenance of glass properties, and the Y-90 activity can be adjusted by Y-90 to Y-89 ratio. Other cations (such as sodium, iron and zinc) can also play a role in terms of controlling the release of yttrium and in the eventual complete bioresorption of microspheres.

The starting calcium metaphosphate (CMP) glass composition is identified (see Group I in Table I).

TABLE I

Examples of the Glass Compositions

| Group | Composition (mol %) | Design Principle |
|---|---|---|
| I | CaO = 50.0, $P_2O_5$ = 50.0 | Calcium metaphosphate, the base composition |
| II | CaO = 50.0, $P_2O_5$ = 50.0 $Y_2O_3$ = 0.5, 1, 2, 4, 8 | This design studies the solubility of $Y_2O_3$ in calcium metaphosphate glasses. Evaluation criteria includes homogeneity of yttrium in glass, crystallization, phase separation, etc. |
| III | CaO = 40-70, $P_2O_5$ = 30-60 $R_2O$ + RO + $R_2O_3$ = 2-15 $Y_2O_3$ = 0, 0.25, 0.5, 1, 2 | This design matrix determined the CaO to $P_2O_5$ ratio varied at 3 levels. Other components and their mixing effect were considered in the design matrix. Effect of $Y_2O_3$ is also included. Note: R stands for Na, Li, K, Ba, Mg, Zn, Sr, Fe, etc. |
| IV | $P_2O_5$ = 30-60 $R_2O$ + RO + $R_2O_3$ = 40-70 Others = 0-10 | This glass composition group mirrors the Group III composition above. The focus was on the replacement of Ca in part or whole with other elements (e.g., Fe, Gd for imaging or diagnostics), and the replacement of Y with other radioisotopes or radioisotope combinations (e.g., Pd, Y + In). Note: R stands for Na, Li, K, Ca, Ba, Mg, Zn, Sr, Fe, Ga, Al, etc. Others include Y, Pd, Ce, Gd, Se, Au, In, Ge, Sm, Ho, Er, Dy, Re, Tl, Yb, Lu, I, Tc, etc. |
| V | $P_2O_5$ + $B_2O_3$ = 30-95 $R_2O$ + RO + $R_2O_3$ = 5-70 Others = 0-10 | This glass composition group mirrors the Group IV composition above. The focus was on the replacement of $P_2O_5$ in part or whole with $B_2O_3$. Refer to Group IV for R and others. |
| VI | $P_2O_5$ + $SiO2$ = 30-95 $R_2O$ + RO + $R_2O_3$ = 5-70 Others = 0-10 | This glass composition group mirrors the Group IV composition above. The focus was on the replacement of $P_2O_5$ in part or whole with $SiO_2$. Refer to Group IV for R and others. |

Compositions of Group II in Table I were formulated by introducing yttrium oxide into Group I in order to study the solubility of yttrium in calcium phosphate glasses. Glasses listed in Group III introduces additional considerations which are relevant in the formulation of these glass compositions include minimizing volatilization of phosphorus oxide from a glass melt. All glasses were prepared using reagent grade chemicals. All compositions listed as Group IV mirror the Group III compositions. The focus was on the replacement of Ca in part or whole with other elements (e.g., Fe, Gd for imaging or diagnostics), and the replacement of Y with other radioisotopes or radioisotope combinations (e.g., Pd, Y+In). Compositions listed in Group V and VI mirror those in Group I-IV. The focus in these groups was to replace $P_2O_5$ with either $B_2O_3$ or $SiO_2$.

B) Control and Detection of Radioactivity Release

The release of yttrium or other radioisotopes was controlled through the creation of a durable surface layer (nitrogen rich layer) on the glass microspheres. Collaborating evidence of timed-bioresorption for some calcium phosphate microspheres has been obtained from the weight loss measurement, the measurement of yttrium release into in vitro solutions, and in the chemical profiling of treated glass surfaces. Furthermore, radioactivity leached to aqueous solution was also measured to confirm the release of radioactivity release from particulates.

Various radiation activity and/or dose measurement methods can be employed. For comparative studies, counters were used. For example, beta detectors (Eberline SHP-380B), beta-gamma detectors (Eberline SHP-190A), gamma detectors (Eberline SPA-8) were use extensively in radioactivity release measurement. Radioactivity release into urine or blood stream were measured using liquid scintillation analyzer (Packard Tri-Carb 2900TR). Other radiation activity or dose measurement methods known by those of skill in the art may also be used.

C) Surface Chemical Durability Enhancement for Bioresorption Control

A nitrided particulate surface has been shown to effectively delay the start of the particulate's resorption for up to 100 days in vitro, and potentially longer.

Nitriding kinetics is affected by temperature, time, ammonia partial pressure and glass composition. Typically the partial pressure of ammonia is fixed conveniently at slightly higher than 1 atmospheric pressure to permit ammonia flow over particulates under treatment. The time for nitriding was 6 and 18 hours for each glass composition. The primary nitriding temperature was the softening temperature, which was determined with an indentation method similar to that used for the dilatometric softening temperature. The higher the nitriding temperature, the faster the nitrogen incorporates into the glass. The nitriding temperature and containment are chosen such that undesirable outcomes such as sintering or recrystallization of the particulates are avoided. Resorption rates of microspheres before and after nitrogen doping were measured to evaluate the effectiveness of nitrogen in enhancing the surface chemical durability of the glasses. Shorter treatment time is desirable for radioisotopes with shorter half-life to minimize excessive decay of useful radioactivity during processing.

X-ray Photoelectron Spectroscopy (XPS) analysis of the glass samples was performed for elements such as P, Ca, Ba, Zn, O and N. Since XPS is a surface sensitive analytical method, sputtering was used "to peel off" thin layers of glass so that XPS depth profiling could be obtained. Chemical profiling of nitrided glass surfaces was done using larger pieces of glass cast from a glass melt. The free surface (i.e., air quenched surface) was used to represent the surface of glass microspheres. The sputtering depth for most samples was such that the entire modified surface layer (due to surface treatment) was "peeled off" until the nitrogen profile was that of the background, that is, the interior of the glass matrix.

Extending the nitriding treatment time from 6 hours to 18 hours more than doubled the initial delay in the start of bioresorption for this calcium phosphate based glass (XLG0153 glass). However, longer treatment time causes an unnecessary delay of usage, hence decay of radioactivity, particularly if the radioisotope already encapsulated the microspheres has relatively short half life. For example, nitriding microspheres containing Y-90 for 64 hours may create longer delay in the start of bioresorption, however, 50% of the original Y-90 activity will be decayed during the treatment. It is preferred to use the highest possible treatment temperature to shorten the treatment time while achieving longer delay in the start of bioresorption.

Figure 8A:
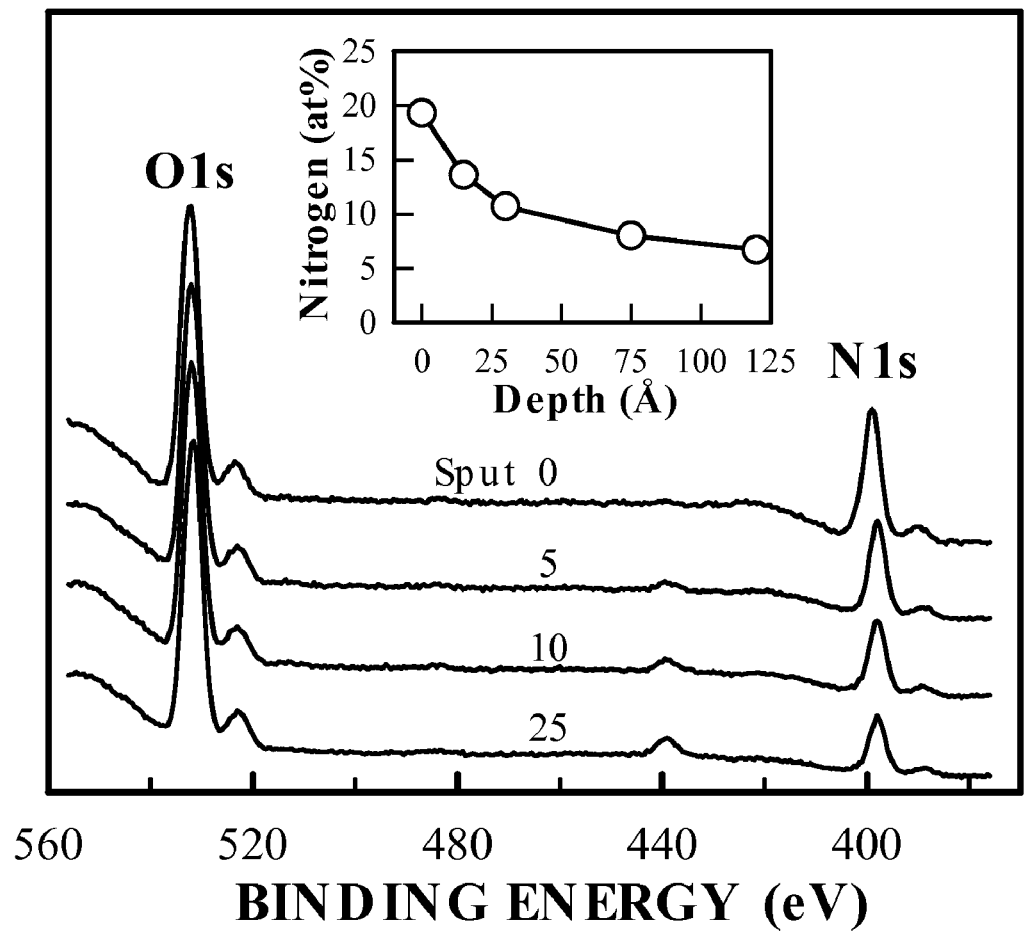
FIG. 8(A) shows XPS O1s and N1s step profiles of one of the thicker nitrogen-containing layers on XLG0101 glass surface after nitriding in ammonia at 518° C. for 24 hours. The insert graph in (A) is nitrogen content in atomic percent based on the entire survey spectrum which included all elements in the glass.
Figure 8B:
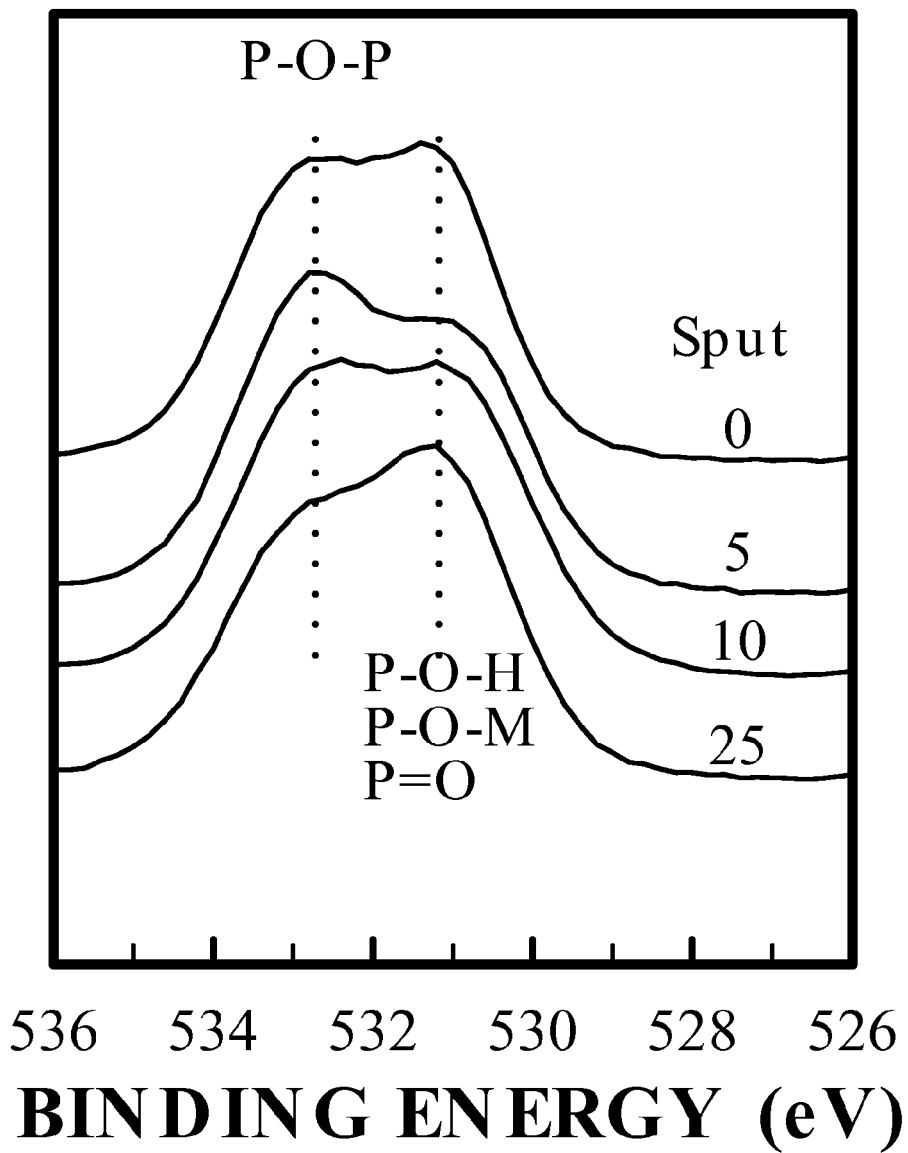
FIG. 8(B) shows the content of bridging oxygen (P—O—P) and non-bridging oxygen in the first 15 Å surface layer.

Direct corroborating evidence of the effectiveness of the surface treatment is the surface chemistry measurement. XPS depth profiling of nitrided glasses indicated that there was indeed a glass surface layer enriched with nitrogen. This layer was typically 10 to 50 Å deep. One of the thicker nitrogen-containing layers (see FIG. 8A) was found on glass XLG0101 surface after nitriding in ammonia at 518° C. for 24 hours. Note that a nitrogen concentration as high as 20 atom % was found in the surface layer. FIG. 8B also indicates that in the first 15 Å surface layer, the content of bridging oxygen (P—O—P) is higher, suggesting that nitrogen replaces non-bridging oxygen species such as P—OH, P=O. The removal of —OH in a phosphate glass as a result of nitriding was also confirmed qualitatively using infrared spectroscopy.

Figure 3:
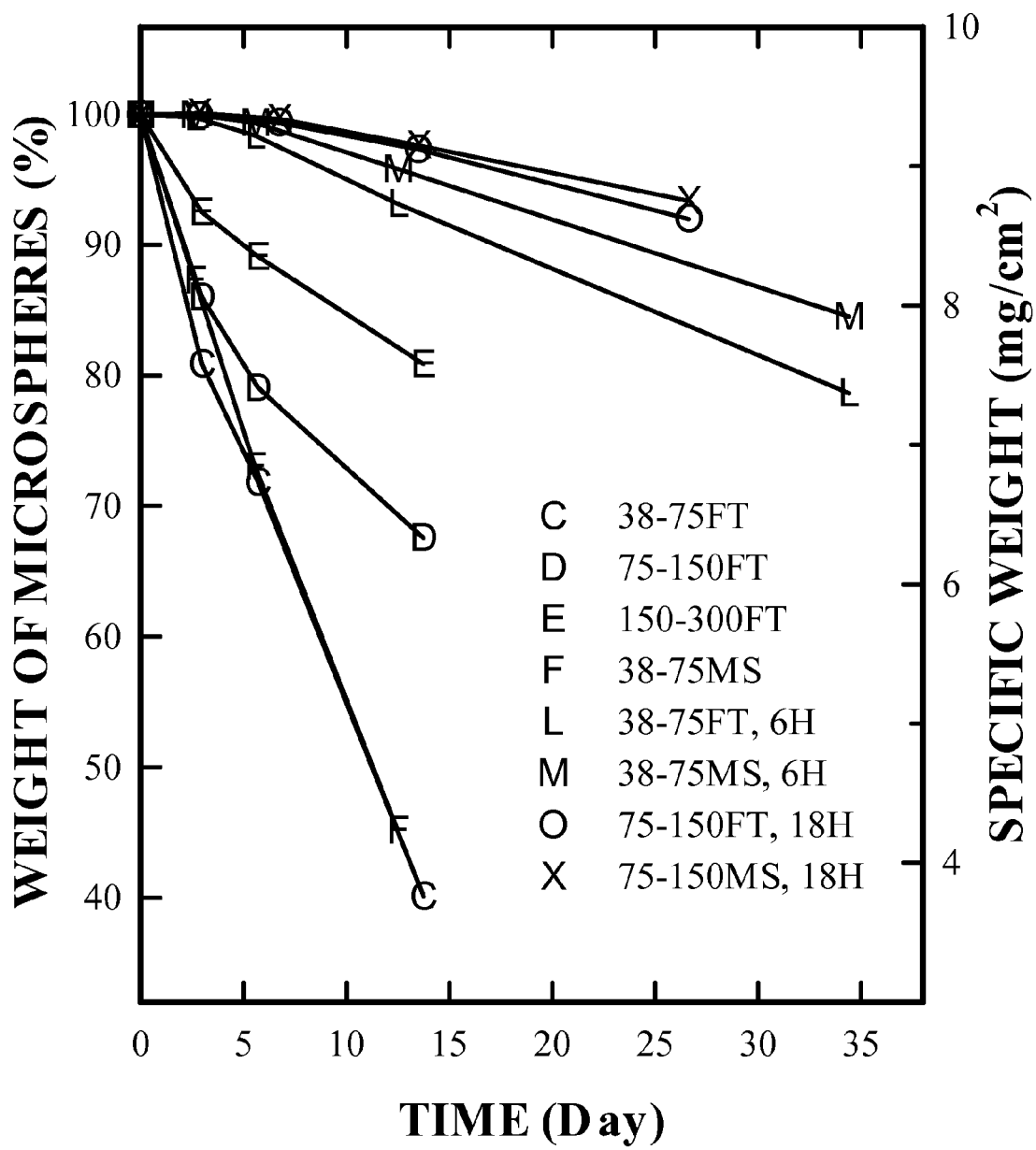
FIG. 3 shows relative bioresorption rates as functions of particle size, particle shape, and surface treatment. "C", "D", and "E" are glass frit of sizes 38 to 75 µm, 75 to 150 µm, and 150 to 300 µm, respectively "F" represents glass microspheres of 38 to 75 µm. "L" and "M" are 38 to 75 µm glass frit and glass microspheres, respectively, after 6-hour treatment. "O" and "X" are 75 to 150 µm glass frit and glass microspheres, respectively, after 18-hour treatment. The glasses contain 1 mol % $Y_2O_3$ and 93.5 mol % of $CaO+P_2O_5$.
Figure 4A:
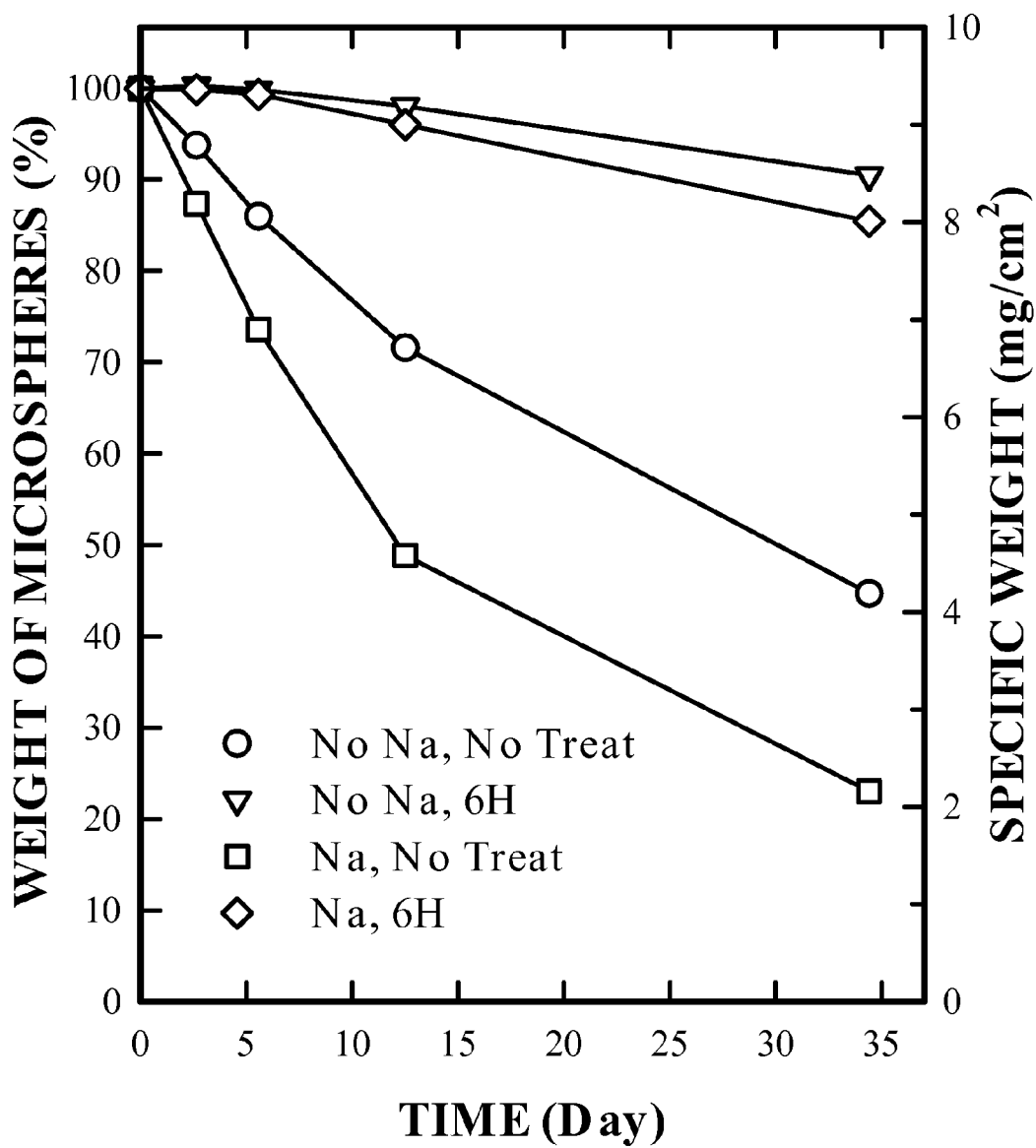
FIG. 4(A) shows the effect of $Na_2O$ on the base bioresorption rate and effectiveness of surface treatment.
Figure 4B:
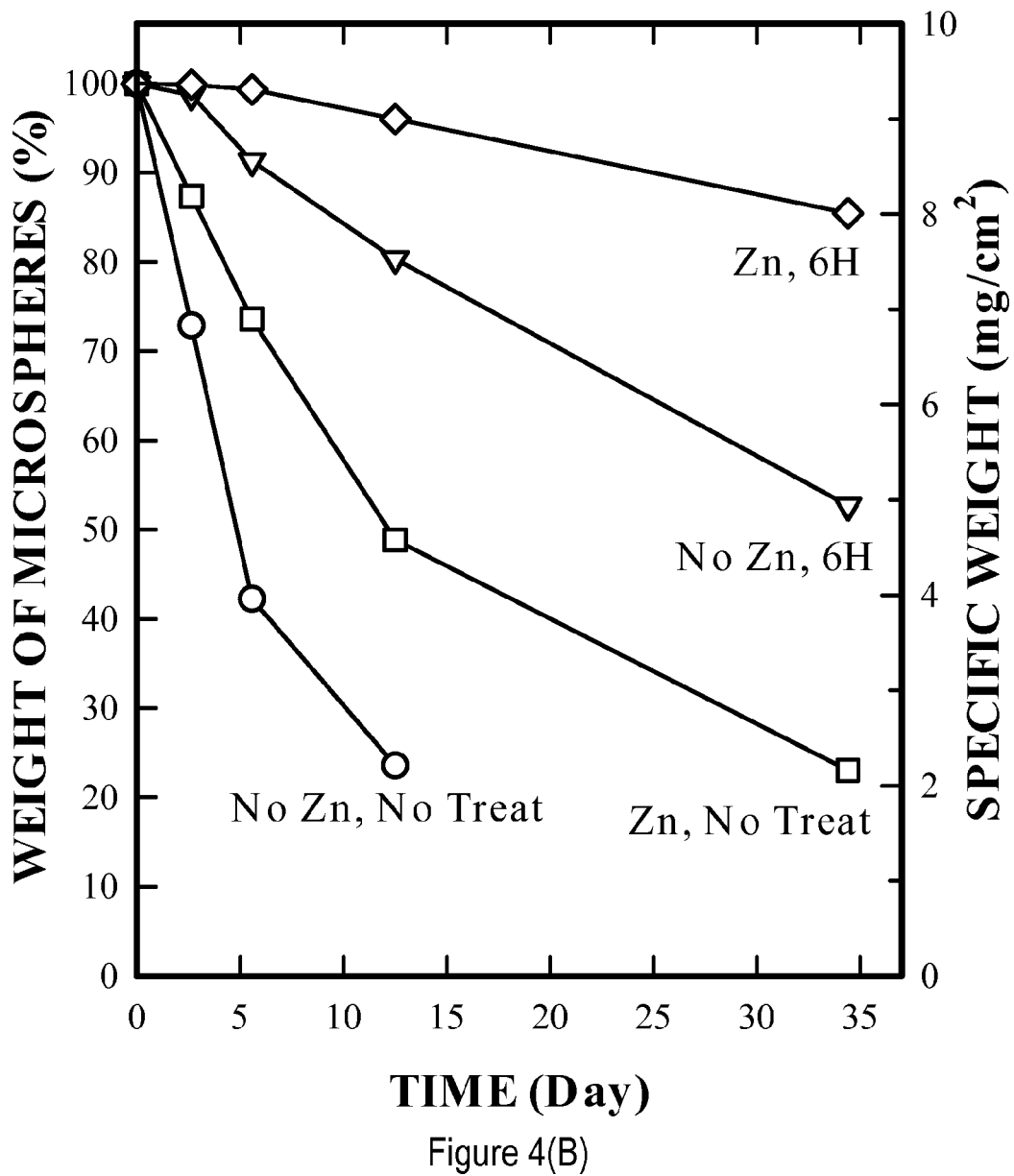
FIG. 4(B) shows bioresorption curves for glass microspheres, untreated and treated for 6 hours, respectively.

XPS depth profiles can explain the early delay in bioresorption or slow bioresorption rate at the beginning. Microspheres would not resorb or dissolve until the surface erosion starts. Since the surface layer of treated particulates has increased bridging oxygen (P—O—P) and decreased non-bridging oxygen, the surface glass layer is more cross-linked in the phosphate chain due to the trivalent nature of nitrogen. It takes a definable period of time for this layer to completely hydrolyze before water can penetrate into the interior of the particulates. The delay in start of bioresorption depends on the thickness of the layer and the nitrogen doping level in this layer. An ideal surface layer treatment approach would combine a high nitrogen doping level and a controllable thickness of surface layer to achieve any predetermined length of delay in bioresorption. The increase in bridging oxygen (P—O—P) or the decrease in non-bridging oxygen in the surface layer potentially accounts for the initial slow bioresorption rates for all surface nitrided particulates as seen in FIGS. 3, 4, and 5. A slower bioresorption rate at the beginning helps to minimize the radioactivity leakage due to bioresorption. Some surface nitrided calcium phosphate particulates (e.g., fibers) with part of the calcium replaced by iron have slow bioresorption rates for over 100 days; this is quite desirable in preventing radioactivity leakage while ensuring the long-term bioresorption. Ideally, there would be no leakage if the bioresorption starts a radioisotope is considered decayed after 10 half-lives of the radioisotope. In the case of Y-90, majority of the radioactivity is decayed after 15 days, see FIG. 9.

Figure 9:
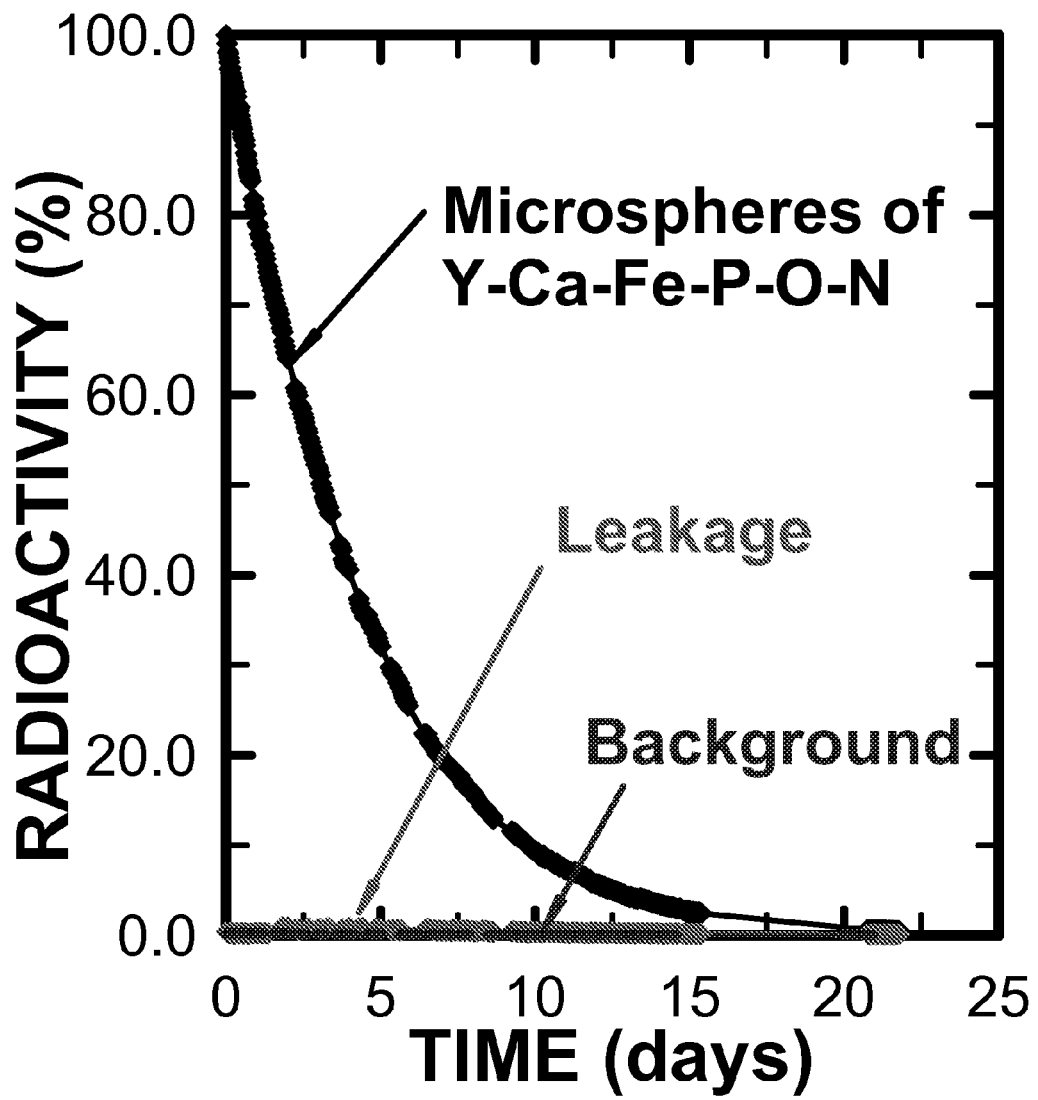
FIG. 9 shows the percentage leakage of radioactivity of Y-90 from thicker microspheres.

FIG. 9 shows measured radioactivity leakage from Y—Ca—Fe—P—O—N glass microspheres. Since measured activity leakage is essentially at the same level as background radiation level, there is no significant leakage of Y-90 during the first 3 to 4 weeks. Note since Y-90 has relatively short half life (2.7 days), there will not be significant activity leakage if the microspheres start to resorb after 3 to 4 weeks.

D) Bioresorption Of Base Glass Matrix

The characterization of bioresorption behavior of microspheres is very indicative of the radiation leaching of Y-90 microspheres. Since Y-90 has a very short half-life (64 hours), Y-90 is considered practically no longer radioactive after 2 to 4 weeks (Note: Y-90 decays to less than 0.03% of its initial activity after 4 weeks). Most of the early screening was also done using glass frit (non-spherical particulates), instead of glass microspheres. Early surface treatments were done using glass frit as well. Our results showed that glass frit simulated glass microspheres reasonably well in characterizing the rate of bioresorption and the effect of surface treatment on the rate of bioresorption. A typical example is given in FIG. 3. The glass was identified as XLG0153 which contains 1 mol % $Y_2O_3$ and 93.5 mol % of $CaO+P_2O_5$, and which belongs to Group III in Table I. The curves labeled "C" and "F" correspond to glass frit and microspheres, respectively, both 38 to 75 µm. These two curves are indistinguishable after 6 days. The same general agreement was also found in nearly all other glasses when comparing frit and microspheres of the same particle size range.

Bioresorption of glass microspheres was characterized by monitoring the weight loss of microspheres and analyzing the in vitro solution using Inductively Coupled Plasma (ICP). Glass microspheres were packed in water-permeable bags with openings of 8 µm, much smaller than microspheres (38-300 µm), but large enough to ensure adequate flow of an in vitro solution into or out of the bags. The in vitro medium solution was a phosphate buffered saline. In general, microspheres were immersed in the medium solutions for a predetermined period of time at 37.5° C. Then the microspheres were taken out for weight loss determination. In vitro medium solution exposed to glass microspheres were kept for ICP analysis and a fresh solution was used for each bioresorption determination. Weight loss measurements were repeated until at least 10-30% of the weight was lost. The glass particles remaining in the bag, if any, were analyzed for assessing the biodegradation mechanism and microstructure. Typically, the in vitro solution volume was fixed at 100 ml. The amount of glass in a package was in the range 0.8 to 1.2 g. Automatic shaking baths were used to insure sufficient medium flow through the bags.

Analyses of in vitro solutions were performed using a Thermo Jarrell Ash IRIS/AP Inductively Coupled Argon Plasma (ICP) analyzer. The analytical protocol used was similar to EPA Test Methods 200.7 "Inductively Coupled Plasma—Atomic Emission Spectroscopy Method for Trace Element Analysis of Water and Wastes." Samples were diluted (when necessary) and acidified to 2 vol % $HNO_3$. prior to introduction to the instrument. Acidification of the samples was performed to ensure that analyte metal ions would remain in solution. Acidification was also required so that the solution could be compared directly with calibration standards which have the same degree of acidification.

Glass compositions were designed to provide a wide range of bioresorption rates. The starting base glass composition was calcium metaphosphate (CMP, Group I in Table I). CMP, a known food additive, is both resorbable and biocompatible.

Five glass compositions were designed in a geometric series, with the highest $Y_2O_3$ up to 8 mol %, listed as Group II in Table I. The first 4 glass compositions formed clear and homogeneous glasses, while the last compositions ($Y_2O_3$=mol %) crystallized during casting. Our calculations indicated that microspheres containing 0.25 mol % $Y_2O_3$ or higher may be used to deliver almost any desirable level of Y-90 radioactivity for radiotherapy. For example, more than 50 curies of Y-90 may be encapsulated in 100 milligrams of glass which contains not more 0.25 mol % of $Y_2O_3$. Since the highest $Y_2O_3$ content, among all the sample glasses spheroidized, reached at least 4 mol %, it is reasonable to expect these glasses to be good matrix for Y-90 to deliver, when necessary, extremely high doses of localized radiation.

Figure 2A:
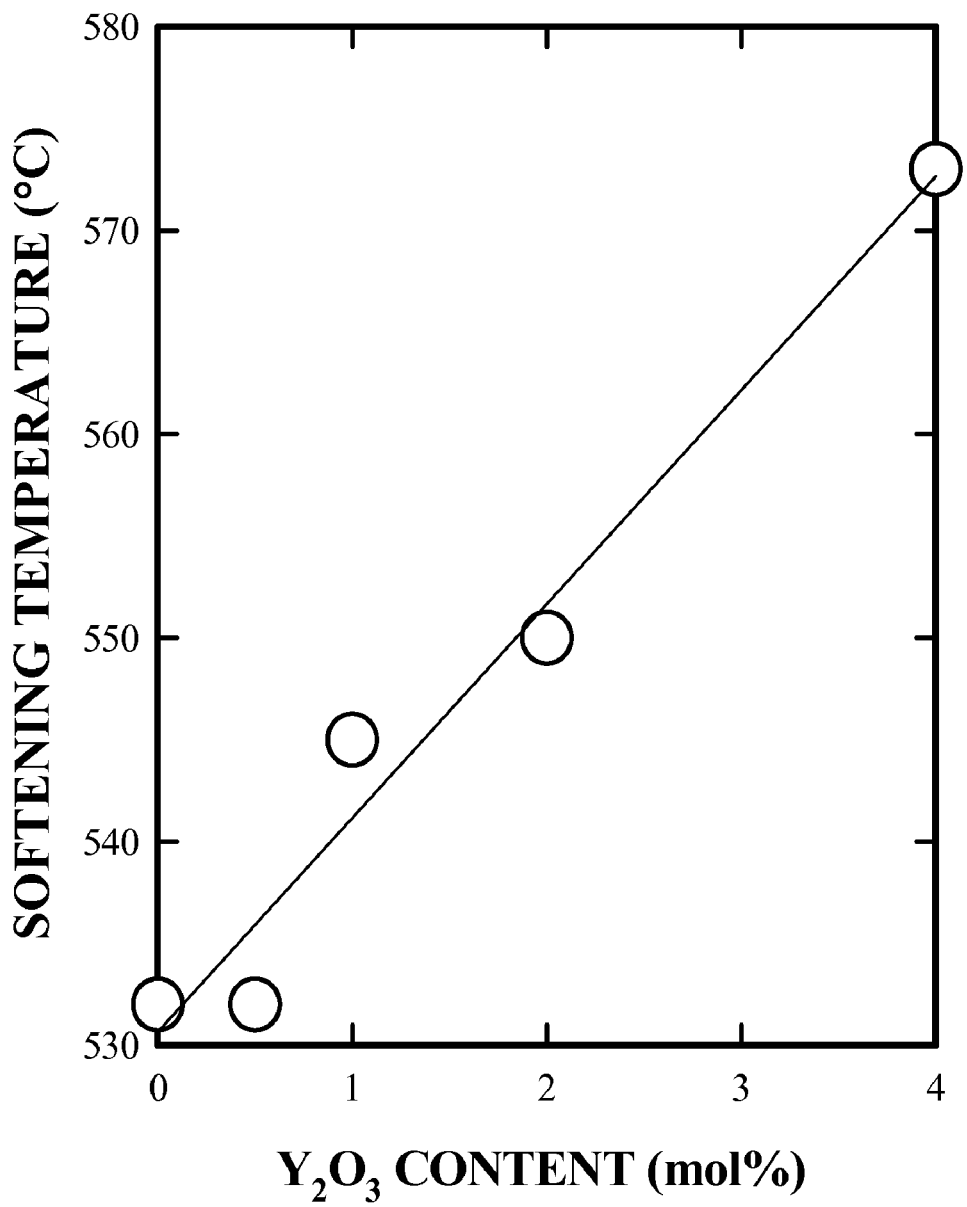
FIG. 2(A) shows the glass softening temperature as a function of $Y_2O_3$ contents, and the effect of $Y_2O_3$ on the softening temperature.
Figure 2B:
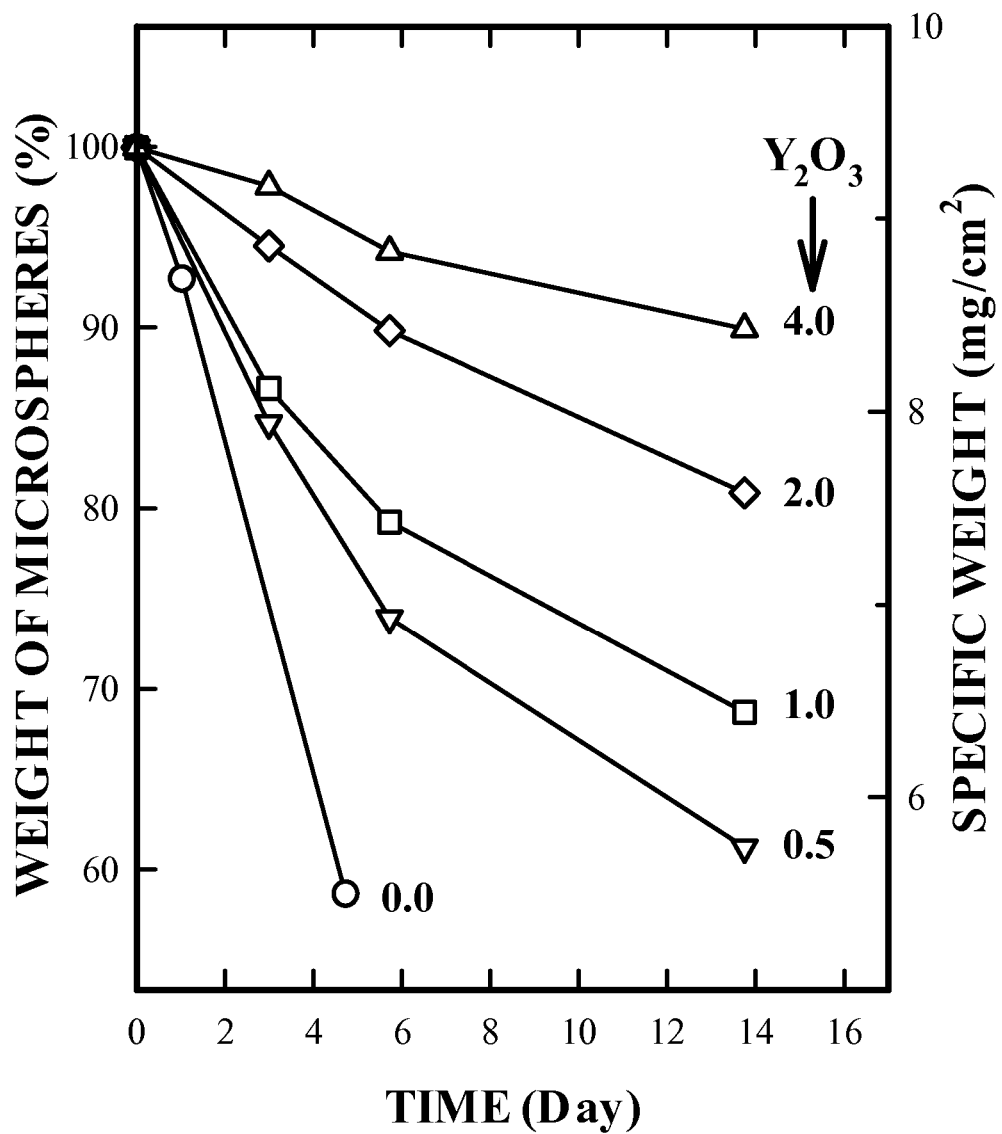
FIG. 2(B) shows the bioresorption in terms of percent weight remaining over time and the effect of $Y_2O_3$ on the bioresorption rates. The label for each line in FIG. 2(B) represents $Y_2O_3$ content in mol %. Glass frit of 150 to 300 µm in size were used for these weight loss measurements in (standard) phosphate buffered saline solution.

Like other high valence cation oxides, such as $Al_2O_3$, $Fe_2O_3$, the introduction of $Y_2O_3$ into the calcium metaphosphate glasses enhances the cross-linking between the phosphate chains, and hence increases the glass softening temperature and slows down the rate of bioresorption. FIG. 2(A) shows the glass softening temperature as a function of $Y_2O_3$ contents. There is over a 40° C. increase in the softening temperature, which indicates a significant glass property change at higher $Y_2O_3$ contents. FIG. 2(B) expresses the bioresorption in terms of percent weight remaining over time. Even at concentrations of 1 mol % or below, the effect of $Y_2O_3$ on the bioresorption rate of a glass may be observed. See FIG. 2(B) for weight loss curves for $Y_2O_3$=0.5 and 1.0 mol %. At 2 and 4 mol % levels of $Y_2O_3$, the bioresorption rates become much slower. For example, it takes about 12 days for the calcium metaphosphate glass (i.e., glass with $Y_2O_3$=0.0) to resorb completely, while it is likely to take a minimum of 60 days for glass with $Y_2O_3$=2.0 to resorb completely.

The purpose of evaluating glasses listed as Group III in Table I was to obtain one or more glasses that are responsive to the surface treatments. The $CaO/P_2O_5$ ratios in these glass compositions varied from below to above that of calcium metaphosphate, that is Ca/P=1/2. While many additive ingredients were used, the total content of all other oxides was designed to be within the range of 2-15 mol %. A proper ratio of mixed cations such as Na, Ba, Zn, Sr may produce as much as a 100-day delay in bioresorption after a nitriding treatment of particulate surface. Glass compositions listed as Group III in Table I contain 0.25 to 2 mol % $Y_2O_3$. All compositions were melted at a reasonably low temperature (900 to 1300° C.), quenched into homogeneous glasses, and spheroidized. Several glass compositions out of this group represent potentially ideal matrices for timed-bioresorbable glass microspheres. They are discussed in detail in the sections to follow.

As discussed above, in one embodiment, various oxide components are added to the base glass matrix to impart one or more additional desirable properties. By studying the effects of individual oxide components on the overall glass composition (referring preferably to oxides of metals of Group III and Group IV in Table I), it was possible to isolate the effect of individual oxide components, while all other parameters were fixed. Each oxide has a distinct role in the design and evaluation of all the glass compositions in Group III and IV in Table I. The majority of the oxide component studies were designed such that one oxide was to replace the equivalent amount (in mol %) of CaO in another glass under study. FIG. 4(A) shows the effect of $Na_2O$ on the base bioresorption rate and effectiveness of surface treatment. XLG0155 glass contains no $Na_2O$. "No Na, No Treat" line (circle) and "No Na, 6H" line (inverted triangle) in FIG. 4(A) represents bioresorption curves for XLG0155 glass microspheres, untreated and treated for 6 hours, respectively. XLG0158 glass contains $Na_2O$. It was prepared by replacing 2.3 mol % of CaO in XLG0155 with 2.3 mol % of $Na_2O$. "Na, No Treat" line (square) and "Na, 6H" line (diamond) in FIG. 4(B) represent bioresorption curves for XLG0158 glass microspheres, untreated and treated for 6 hours, respectively. The introduction of $Na_2O$ into a calcium phosphate glass, as expected, increased the base bioresorption rate (compare curve with circle to that with square). The surface treatment was still very effective in controlling the early bioresorption rate according to FIG. 4(B). Our study indicated that after extensive replacement of CaO by $Na_2O$ (e.g. 25 mol % or more), the surface treatment created a delay in bioresorption of no more than 3 days.

ZnO both influences the base bioresorption rate and enhances the effectiveness of surface treatment. As a result, the delay in the start of bioresorption was extended with the addition of ZnO. XLG0168 glass contained no ZnO. "No Zn, No Treat" line (circle) and "No Zn, 6H" line (inverted triangle) in FIG. 4(B) represent bioresorption curves for XLG0168 glass microspheres, untreated and treated for 6 hours, respectively. Comparisons were also made with XLG0158 which was prepared by replacing 5.6 mol % CaO in XLG0168 with 5.6 mol % of ZnO. "Zn, No Treat" line (square) and "Zn, 6H" line (diamond) in FIG. 4(A) represent bioresorption curves for XLG0158 glass microspheres, untreated and treated for 6 hours, respectively. It may be seen from FIG. 4(B) that replacing CaO with ZnO in a calcium phosphate glass reduced the bioresorption rate. The presence of ZnO in XLG0158, together with surface treatment, effectively controlled the early bioresorption. As will be discussed, Y-90 leakage is minimal when the early bioresorption may be avoided.

Based on the data presented in FIG. 4, one may conclude that by modifying calcium metaphosphate with $Na_2O$ and ZnO, along with appropriate surface treatment, a wide range of bioresorption rates may be obtained. More importantly, one may design the length of the initial delay in the start of bioresorption. Roles for other oxides (BaO, SrO, MgO, etc.) were similarly studied.

In order for the glass microspheres to maintain the intended structural integrity and exhibit minimal impact from the introduction of Y-90 or decay of Y-90, the yttrium level was designed in all of the glasses to be at least 10 to 500 times higher than the required level of Y-90 in glass microspheres for therapeutic use. This allows use of both Y-89 and Y-90 in glass microspheres at any desired ratio while maintaining the same overall chemical or structural yttrium level in a given glass. When presence of Y-89 is dominant in a glass, the effect of Y-90 on the glass structural integrity and bioresorption rate is minimized and predictable. A high Y-89 concentration in a glass is advantageous for additional reasons: (a) it enhances the detection of yttrium using ICP; (b) the release of Y-89 reflects directly on the bioresorption of the microspheres (since ICP measures the Y-89 which comes out of the glass); and (c) it avoids costly and labor-intensive high dose radiation handling during microspheres development. $P_2O_5$, $Y_2O_3$ and CaO are common oxide components in all the glasses listed as Group III in Table I. Since the in vitro media contained phosphates, only Y and Ca became unique elements. Direct measurement of Y and Ca with ICP offered an independent method to validate the large collections of bioresorption data collected using weight loss measurement. Ba, Zn and other cation contents were used to supplement Y and Ca data. The discussion below focuses on selected ICP results for Y and Ca in terms of Y-90 retention and bioresorption of glass microspheres.

Figure 5A:
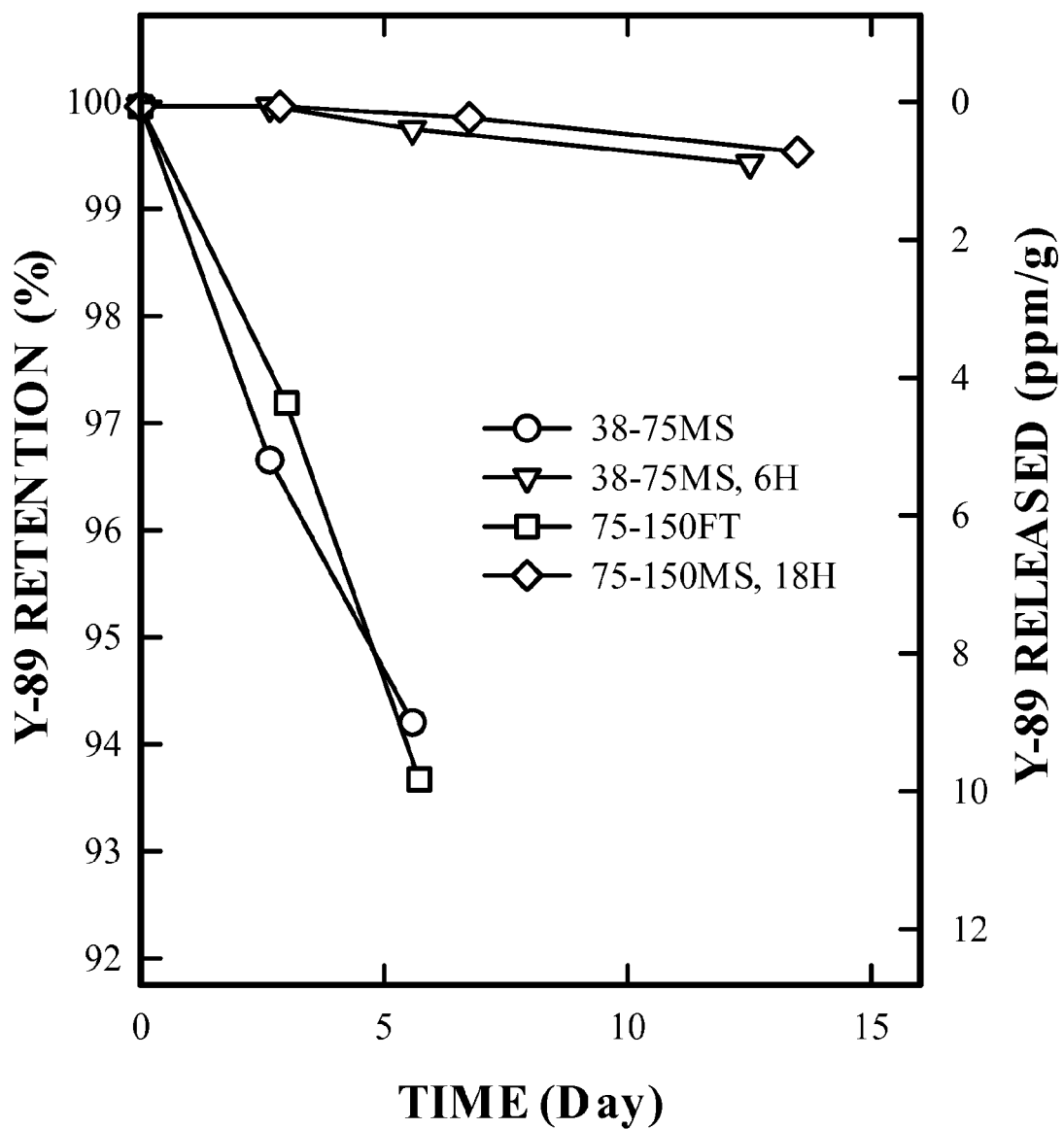
FIG. 5(A) shows the release rates of Y-89.
Figure 5B:
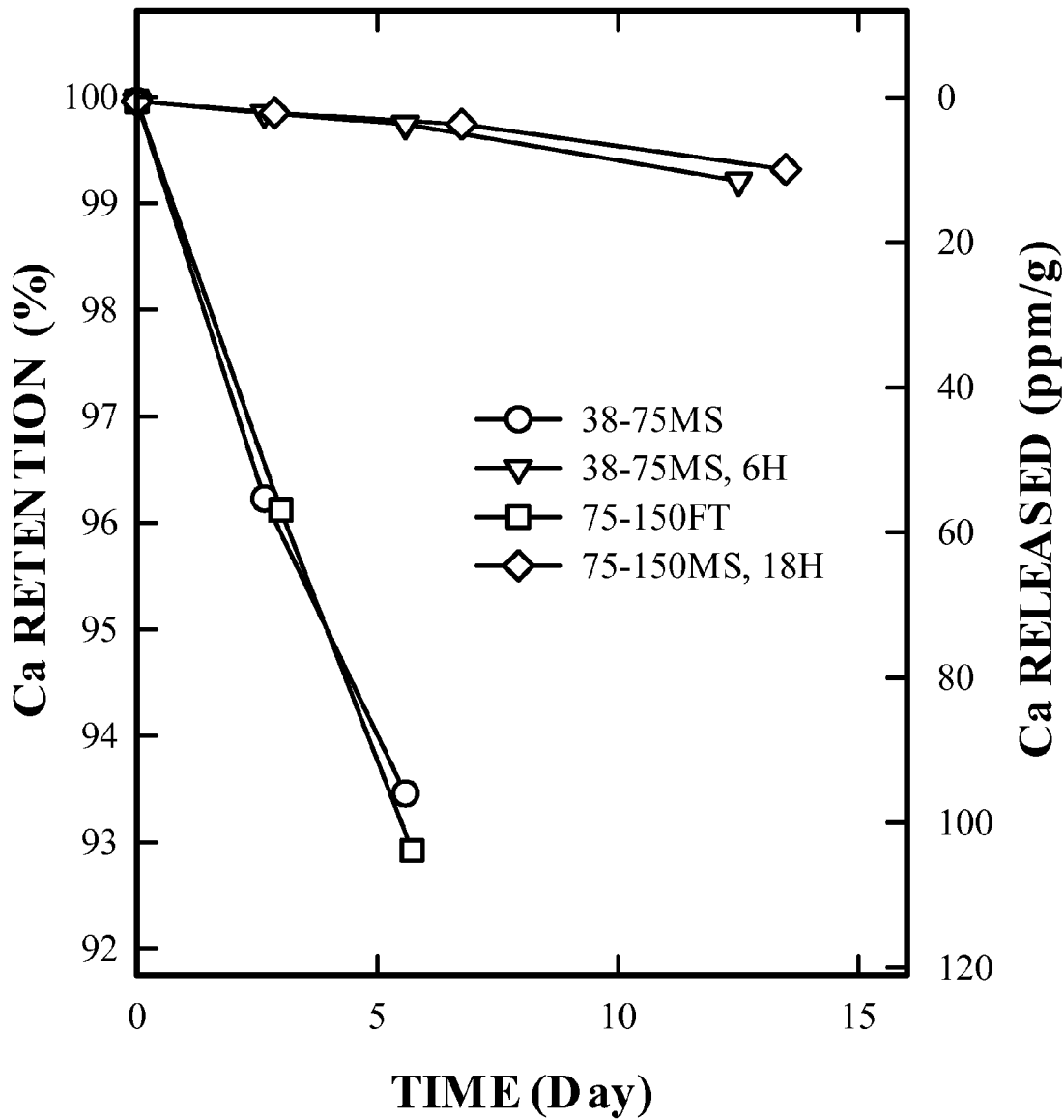
FIG. 5(B) shows the release rates of Ca. Both Y-89 and Ca release were normalized to cumulative ppm in 100 ml in vitro solution and 1 gram of microspheres.

FIGS. 5(A) and (B) compare the release rates of Y-89 and Ca. While the absolute ppm concentration levels in an in vitro solution were quite different between Y-89 and Ca (notice the vertical axes in FIGS. 5(A) and (B)), the relative release rates were nearly identical, indicating a uniform bioresorption of glass microspheres. Bioresorption rates measured using weight loss were generally in excellent agreement with ICP measurement. While ICP and weight loss measurements complement each other, ICP is nevertheless the direct measure of Y-90 or Y-89 release. Weight loss measurements were effective to monitor the long term bioresorption of microspheres.

Considering the radioactive decay of Y-90, the effective Y-90 retentions were calculated based on the Y-89 ICP data.

Figure 6:
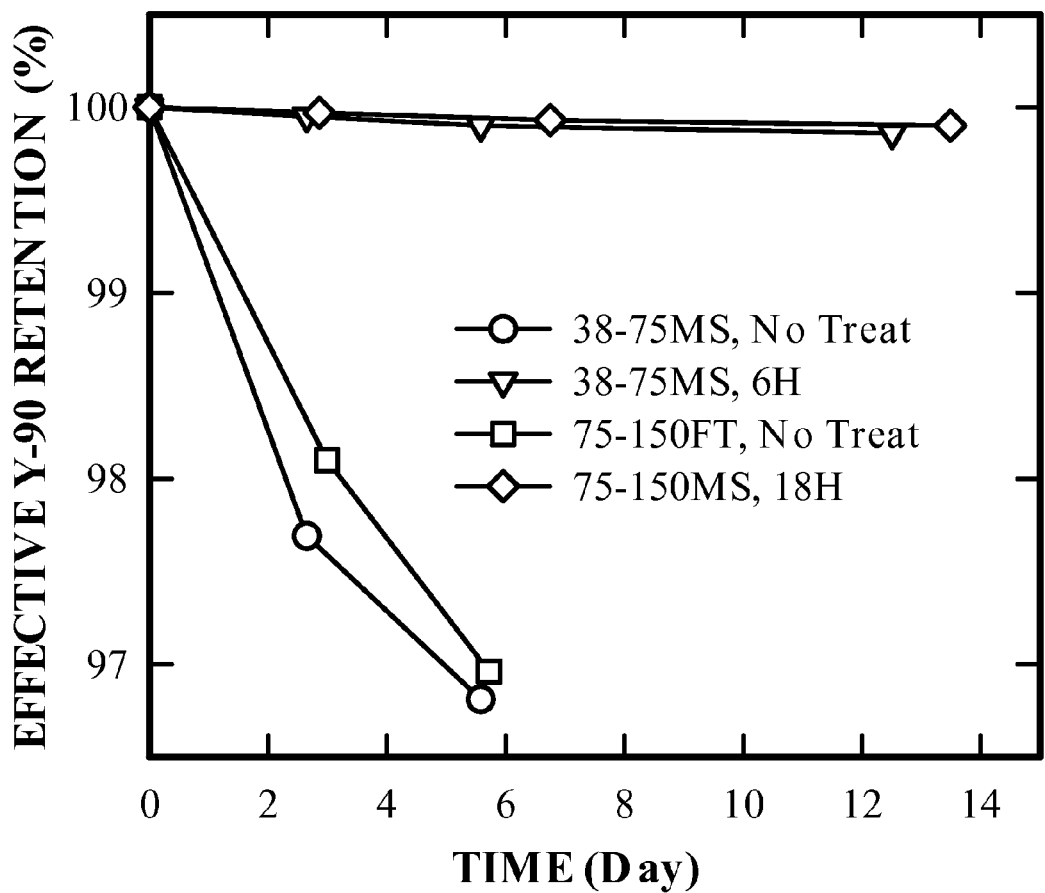
FIG. 6 shows the effective percentage retention of Y-90 in XLG0157 glass microspheres based on Y-89 ICP data presented in FIG. 5(A), taking into account of natural decay of Y-90 with half-life of 64 hours.

An example of such calculation is presented in FIG. 6 using ICP data presented in FIG. 5(A). XLG0157 glass microspheres after surface treatment retained over 99% of yttrium during the first two weeks (See FIG. 5(A)). When the radioactive decay effect is factored in, nearly 99.9% of Y-90 is retainable within the microspheres. Microspheres of XLG0154, XLG0158, XLG0164 also retained yttrium effectively after they were surface treated.

Figure 7:
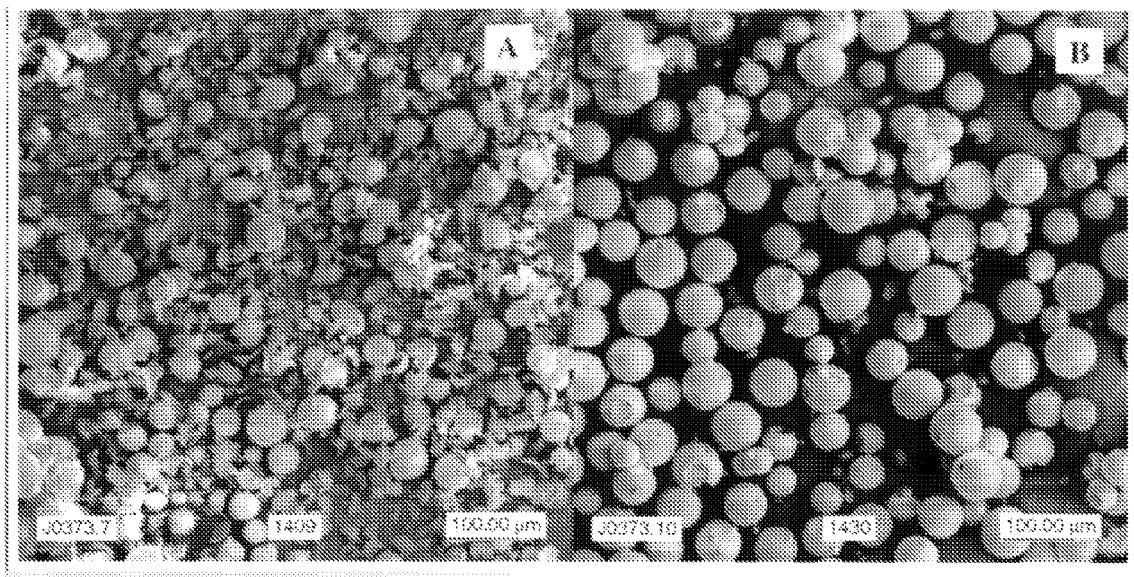
FIG. 7(A) shows microspheres of 38-75 µm in size after 34 days in vitro at 37.5° C.
FIG. 7(B) shows microspheres corresponding to the last data point on the "Na, 6H" line in FIG. 4(A), according to which there had been a 15% weight loss. The effect of surface treatment on bioresorption rate and mechanism: (A) untreated and (B) treated for 6 hours. SEM micrographs (A) and (B) were both taken after 34 days in vitro. Glass was XLG0158 and the size of microspheres was 38-75 µm.

There is also SEM evidence on bioresorption of glass microspheres and the effect of surface treatment in controlling the early bioresorption rates. FIG. 1(B) shows XLG0158 microspheres, 38-75 μm in size. These microspheres are shown as prepared, without any surface treatment, and before the bioresorption test. FIG. 7(A) shows the same microspheres after 34 days in vitro at 37.5° C. The biodegradation, i.e., bioresorption, is obvious. These microspheres correspond to the last data point on the "Na, No Treat" line in FIG. 4(A). There was about 70% weight loss within 34 days in vitro, according to FIG. 4(A). When the same microspheres were surface treated for 6 hours, the early bioresorption was controlled. After 34 days in vitro, most of the microspheres were still intact, although the start of biodegradation may be easily identified (see FIG. 7(B)). Microspheres shown in FIG. 7(B) correspond to the last data point on the "Na, 6H" line in FIG. 4(A), according to which there had been a 15% weight loss. Other glass microspheres confirmed the same general trend in bioresorption rate and mechanism. The surface treatment delayed the start of bioresorption in vitro for all glasses listed in Table I.

E) Spheroidization Process and Control

The feasibility of making calcium phosphate glass microspheres in a restricted and radiologically controlled space has been demonstrated.

Glasses (e.g., bulk glasses from glass melts) which are chemically homogeneous were first pulverized and classified into specific size ranges. Frit larger than a specified size may be re-pulverized and classified. To demonstrate the range of all feasible microspheres of a given base glass matrix, the bulk glass is pulverized and classified into 3 major size groups: less than 75 μm, 75-150 μm, and greater than 150 μm. These powders were stored under dry nitrogen before the spheroidization process. The spheroidization process was carried out by suspending glass frit in a high temperature chamber so that the frit had sufficient time to melt and form spherical liquid droplets before exiting high temperature chamber. When the liquid glass drops were cooled, they solidified into glass microspheres. For example, glass powders were dropped into a heated vertical tube. As powders fell through the heated zone (usually the middle portion of the tube, temperatures were typically 900° C. to 1800° C.), they were heated and melted into individual melted droplets. These droplets were quenched and solidified into solid microspheres when they exited the vertical tube. The length and the temperature distribution of the heat zone and the additional quenching at the exit end were adjusted such that all powders were spheroidized with minimal or no overheating and droplet collision. The glass viscosity-temperature relationships provide useful information for spheroidization. Microspheres produced using the disclosed method ranges from submicron to over 1 mm.

Other methods of spheroidization are possible for a given phosphate glass composition. For example, homogeneous phosphate particulates, especially microspheres, are also prepared without melting bulk glasses. In one preferred method, all necessary phosphate glass components are dissolved into a chemically homogeneous solution (typically acidic solution, e.g. dilute nitric acid). Such solution is first converted into dry particulates of desired particle mass or size by evaporating part or all of the volatile components of solution particulates (e.g. atomized solution droplets). In another method, all necessary borate glass components may also be dissolved into a chemically homogeneous solution. In the case of silicate glasses, the solution may contain not aqueous solvents and may contain silica colloids homogeneously suspended in solution. Further solidification of the dry particulates form solid, or porous, or hollow microspheres. Based on well-known powder metallurgy and ceramic processing principles, solidification of a spherical particle to spheres require relatively lower temperature than that is required to convert glass frit into glass microspheres. Additionally, appropriate control of both the drying parameters and the solidification parameters results in desirable densities of the final microspheres by controlling the porosities or void space entrapped inside glass microspheres. These example process steps (solution, dry powder and solidification) may be performed as individual steps or integrated in a continuous succession for a person skilled in the art. In these and other methods of preparing base glass matrices without melting bulk glasses, radioisotopes or a combination of radioisotopes may be incorporated. For example, a radioactive isotope or combination of radioisotopes may be added to the chemically homogeneous solution discussed above. The resultant particulates have the radioactive isotope or radioisotope combination incorporated directly and homogeneously within the particulate, and does not require additional activation, e.g., by high energy particle irradiation via a neutron beam, an accelerator or other means. Individual microspheres prepared using the method have a density varying from lower than that of water. (e.g., floating in water about 0.4 grams/mL) to the maximum density of the void-fee solid glass (about 2.8 grams/mL). For the best dispersion of microspheres by the body fluid (e.g., blood, synovial fluid), it is preferred that the density of the microspheres be close to that of the fluid (typically 0.4 to 2.0 grams/mL, preferably 0.8 to 1.2 grams/mL), and the size be as small as permissible for the therapy or diagnostics. The density of microspheres is of particular importance when larger diameter spheres are used for embolization of blood flow or the flow of other body fluid. When the diameter is larger than 50 micrometers, it is preferred to have the density of microspheres closely matching that of the body fluid to be embolized. It is also noted that microspheres intended for embolization may not contain radioisotopes. But the combination of microspheres and therapeutic radioisotopes in the form of radio-embolization is preferable. The use of a radiotracer such as In-111 or Tc-99m is also desirable for locating the microspheres and/or mapping the flow of the body fluid to be embolized.

FIG. 1 shows typical glass frit (A) of size 38 to 75 μm, and typical microspheres (B) after spheroidization. While it is possible to classify these microspheres into very narrow size distributions such as FIGS. 1 (C) and (D) for 38 and 75 microns, respectively, the common size ranges were 5 μm or less, 5 to 15 μm, 15 to 38 μm, 38 to 75 μm, 75 to 150 μm, 150 to 300 μm, and other size ranges. Important properties of microspheres evaluated include the bioresorption rate and profile, toxicity, retention of radioactivity, density, etc. Relevant properties are measured and selected properties are discussed as non-limiting examples.

There are several possible ways to prepare glass microspheres. However, methods useful for Y-90 microspheres preferably utilize lower processing temperatures and keep all radiative material contained throughout the spheroidization process.

F) Biocompatibility Of Base Glass Matrix

Biocompatibility studies of yttrium-containing microspheres served as a preliminary screening, with a primary focus on the effect of $Y_2O_3$ addition to a glass and that of surface treatment. Microspheres of two glasses, XLG0168 and XLG0155, are listed as examples out of a total of eight tested. All microspheres contained 1 mol % $Y_2O_3$ and were surface treated for 18 hours. Grade 2 or below is considered non-toxic. XLG0168 and XLG0155, along with others, received a grade 0. Microspheres without $Y_2O_3$ and without surface treatment were not analyzed since biocompatibility is considered an important factor in glass composition design. The preferred glass composition design to ensure good biocompatibility is to understand the potential toxicity of each individual glass component, the tolerance level of each component within the human body, and the potential release rate of a component into the body after implantation. For example, iron (Fe), zinc (Zn) may replace in part or in whole the calcium (Ca) in a base glass composition without causing toxicity since the body has high tolerance. But the body has less tolerance for barium (Ba), significantly less for gadolinium (Gd). In other words, toxicity of glass particulates depends on not only glass chemistry, but the cumulating level of given component within the body.

TABLE II

Cytotoxicity Screening of Microspheres Containing $Y_2O_3$

| Microspheres | Material | % Rounding | % Lysis | Grade | Conclusion |
|---|---|---|---|---|---|
| XLG0168 | Microspheres | 0, 0 | 0, 0 | 0, 0 | Not Toxic, Not Toxic |
|  | Negative Control | 0, 0 | 0, 0 | 0, 0 |  |
|  | Positive Control | 80, 80 | 80, 80 | 4, 4 |  |
| XLG0155 | Microspheres | 0, 0 | 0, 0 | 0, 0 | Not Toxic, Not Toxic |
|  | Negative Control | 0, 0 | 0, 0 | 0, 0 |  |
|  | Positive Control | 80, 80 | 80, 80 | 4, 4 |  |

G) Additional Discussion

The retention of isotopes such as yttrium at the beginning and the eventual complete bioresorption of the phosphate glass matrix make bioresorbable phosphate based microspheres an ideal carrier matrix for radioisotopes such as Y-90 and other isotopes disclosed. The results demonstrate:

1) Phosphate glass based particulates (e.g., microspheres or fibers) can homogeneously dissolve sufficient amounts of yttrium (Y-89, Y-90), and essentially all isotopes of interest and may be suitable for delivery of one or multiple isotope combination for radiotherapy and/or diagnostics. Yttrium content may be as high as 4 mol % (6.4 wt %), and potentially higher. Phosphate based glasses are good hosts for other radioisotopes disclosed at sufficiently high radioactivity level for radiotherapy and/or diagnostics.

2) Doping the surface layer of microspheres with chemical nitrogen can delay the start of bioresorption of phosphate based particulates (e.g., microspheres, fibers). The effectiveness of nitrogen doping is a function of glass composition, treatment time, treatment atmosphere and treatment temperature. Similar effectiveness of nitrogen doping is expected in borate and silicate based glasses since nitrogen has been proven to have the ability replacing all oxygen in $B_2O_3$ to form BN, and all oxygen in $SiO_2$ to form $Si_3N_4$.

3) The bioresorption of phosphate particulates (e.g. microspheres, fibers) in vitro is evident and measurable from weight loss, solution analysis using ICP, microstructural examination using SEM, surface chemical profiling using XPS, and radioactivity measurement from radioisotopes.

4) Spheroidization of phosphate glass microspheres may be done at relatively low glass-making temperatures in a radioactive materials processing zone.

5) Surface treated microspheres containing yttrium are non-toxic. Potential contamination from chemicals and processing is minimal.

Although only preferred embodiments are specifically disclosed and claimed herein, it will be appreciated that further modifications of the invention may be made without departing from the spirit and intended scope of the invention.

What is claimed is:

1. A resorbable implant material for radiotherapy comprising:
   (i) a resorbable base glass matrix which is biocompatible;
   (ii) a radioactive isotope or combination of radioisotopes, wherein said radioisotope or combination of radioisotopes is incorporated or encapsulated directly and homogeneously into the base glass matrix during the process of manufacturing said base glass matrix, and wherein said base glass matrix does not need or require high energy particle irradiation to convert one or more stable isotopes into radioactive isotopes; and
   (iii) a nitrogen-rich surface layer formed on the resorbable base glass matrix, the surface layer being of greater durability than the base glass matrix.

2. A resorbable implant material for radiotherapy comprising:
   (i) a resorbable base glass matrix which is biocompatible;
   (ii) a radioactive isotope or combination of radioisotopes, wherein said radioisotope or combination of radioisotopes is incorporated or encapsulated directly and homogeneously into the base glass matrix; and
   (iii) a nitrogen-rich surface layer formed on the resorbable base glass matrix, the surface layer being of greater durability than the base glass matrix.

3. The resorbable implant material of claim 2, wherein the nitrogen rich surface layer substantially prevents premature release of said radioactive isotope or combination of radioisotopes for up to 10 half-lives of the longest lived radioisotope in said implant.

4. The resorbable implant material of claim 2, wherein said resorbable base glass comprises a silicate, borate or phosphate based matrix.

5. The resorbable implant material of claim 2, wherein said resorbable base glass matrix is a phosphate based matrix.

6. The resorbable implant material of claim 5, wherein said phosphate based matrix comprises phosphate in combination with calcium, zinc, iron, barium, sodium, strontium, magnesium, aluminum, gallium, indium, lithium, potassium, cesium, rubidium, or combinations thereof.

7. The resorbable implant of claim 5, wherein said phosphate based glass matrix comprises a calcium to phosphate ratio from about 0.33 to about 1.67.

8. The resorbable implant material of claim 2, wherein the implant material comprises image enhancing agents suitable for MRI, other imaging agents, diagnostic agents, or combinations thereof.

9. The resorbable implant material of claim 8, wherein the image enhancing agent is gadolinium, iron or combinations thereof.

10. The resorbable implant material of claim 5, wherein at least part of said phosphate based matrix contains a borate or silicate.

11. The resorbable implant material of claim 2, wherein the implant material contains selenium.

12. The resorbable implant material of claim 2, wherein said nitrogen rich surface layer comprises up to about 15 molar % nitrogen.

13. The resorbable implant material of claim 2, wherein said radioactive isotope or combination of radioisotopes is Y-90, In-111, Pd-103, P-32, Cs-131, Sm-153, Ho-166, Tc-99m, Yb-169, Au-198, Re-188, Re-186, Ir-192, Lu-177, Ba-140, Se-72, I-131, I-125, Sr-90, Dy-165, Er, Tl, Sr, Gd, Y-90/In-111, Y-90/Tc-99m, P-32/In-111, P-32/Tc-99m, Ho-166/ In-111, Ho-166/Tc-99m, Sm-153/In-111, Sm-153/Tc-99m, or combinations thereof.

14. The resorbable implant material of claim 13, wherein said radioactive isotope or combination of radioisotopes is present in said base glass matrix in an amount effective for radiation synovectomy of arthritis.

15. The resorbabable implant material of claim 13, wherein said radioactive or combination of radioisotopes is present in said base glass matrix in an amount effective for radiation therapy of a tumor.

16. The resorbable implant material of claim 2, wherein said base glass matrix comprises up to 50 curies of total radioactivity from all isotopes.

17. The resorbable implant material of claim 2, wherein the resorbable base glass matrix is a particulate, microsphere, porous microsphere, hollow microsphere, microcapsule, fiber, short fiber, small rod, particulate dispersed in biopolymers, particulate dispersed in bioresorbable sutures, particulate dispersed in biocompatible gels, particulate dispersed in other media, or combinations thereof.

18. The resorbable implant material of claim 2, wherein said implant is a non-conductive implant.

19. The resorbable implant material of claim 18, wherein said non-conductive implant is radiogaphically detectable.

20. The resorbable implant material of claim 18, wherein said non-conductive implant is embedded in a non-conductive delivery vehicle.

21. The resorbable implant material of claim 20, wherein said non-conductive delivery vehicle is a biopolymer, bioresorbable suture, injectable gel, tissue adhesive, other media, or combinations thereof.

22. The resorbable implant material of claim 21, wherein said biopolymer is poly-l-lactic acid in the molecular weight range of 30,000 to 500,000, poly-l-lactic acid co-polymers with polyglycolic acid, polydioanone (PDS II), polyglycaprone 25 (Moncryl), polyglactin 910 (Vicryl), phenyletheretherketone (PEEK), polysulfone (PSU), polyurethane, polypropylene, silicone, polyethylene terephthalate (PET), polyphenylene oxide blends (PPO), polyphenylsulfone (PPSU), polyether sulfone (PES), polyphenylene sulfide (PPS), polyetherimide (PEI), liquid crystal polymer (LCP), or combinations thereof.

* * * * *